(12) United States Patent
McGowan et al.

(10) Patent No.: US 9,133,192 B2
(45) Date of Patent: Sep. 15, 2015

(54) PIPERIDINO-PYRIMIDINE DERIVATIVES FOR THE TREATMENT OF VIRAL INFECTIONS

(71) Applicant: Janssen R&D Ireland, Little Island, Co Cork (IE)

(72) Inventors: David Craig McGowan, Brussels (BE); Pierre Jean-Marie Bernard Raboisson, Rosieres (BE); Tim Hugo Maria Jonckers, Heist-op-den-Berg (BE); Mourad Daoubi Khamlichi, Murica (ES)

(73) Assignee: JANSSEN SCIENCES IRELAND UC, Little Island, Co. Cork (IL)

( * ) Notice: Subject to any disclaimer, the term of this patent is extended or adjusted under 35 U.S.C. 154(b) by 0 days.

(21) Appl. No.: 14/377,064

(22) PCT Filed: Feb. 7, 2013

(86) PCT No.: PCT/EP2013/052372
§ 371 (c)(1),
(2) Date: Aug. 6, 2014

(87) PCT Pub. No.: WO2013/117615
PCT Pub. Date: Aug. 15, 2013

(65) Prior Publication Data
US 2014/0350031 A1    Nov. 27, 2014

(30) Foreign Application Priority Data
Feb. 8, 2012    (EP) .................................. 12154474

(51) Int. Cl.
C07D 471/04    (2006.01)
A61K 31/529    (2006.01)
A61K 31/519    (2006.01)

(52) U.S. Cl.
CPC ............ *C07D 471/04* (2013.01); *A61K 31/519* (2013.01)

(58) Field of Classification Search
CPC .......................... C07D 471/04; A61K 31/519
USPC ........................................ 544/279; 514/264.1
See application file for complete search history.

(56) References Cited

U.S. PATENT DOCUMENTS 7,524,852 B2 * 4/2009 Arai et al. ................ 514/264.11
8,486,952 B2 * 7/2013 Boy et al. ................... 514/258.1
8,637,525 B2 * 1/2014 Boy et al. ................... 514/258.1

FOREIGN PATENT DOCUMENTS

| EP | 1110951 B1 | 5/2004 |
|----|------------|--------|
| EP | 1552842 A1 | 7/2005 |
| WO | WO 98/01448 A1 | 1/1998 |
| WO | WO 99/28321 A1 | 6/1999 |
| WO | WO 2006/117670 A1 | 11/2006 |
| WO | WO 2009/067081 A1 | 5/2009 |
| WO | WO 2013/117615 A1 | 8/2013 |

OTHER PUBLICATIONS

Vippagunta et al., Advanced Drug Delivery Reviews 48: 3-26, 2001.*
Ulrich J. Kirk-Othmer Encyclopedia of Chemical Technology, John Wiley & Sons, Inc, pp. 1-7, 2002.*
Ohto et al., Microbes and Infection 16 (2014) 273-282.*
Yu et al.<Biochimica et Biophysica Acta 1835 (2013) 144-154.*
Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Zhao et al., Frontiers in Immunology. 5, 1-6,2014.*
Hoffman, J.A.,"The immune response of Drosophila", Nature, 426, pp. 33-38, 2003.
Akira, S. et al., "Toll-Like Receptors", Annual Rev. Immunology, 21, pp. 335-376, 2003.
Ulevitch, R.J., "Therapeutics targeting the innate immune system", Nature Reviews: Immunology, 4, p. 512-520, 2004.
PCT International Search Report and Written Opinion for corresponding International Application No. PCT/EP2013/052372 dated Apr. 17, 2013.

* cited by examiner

*Primary Examiner* — Venkataraman Balasubramanian

(57) ABSTRACT

This invention relates to piperidino-pyhmidine derivatives, processes for their preparation, pharmaceutical compositions, and their use in treating viral infections.

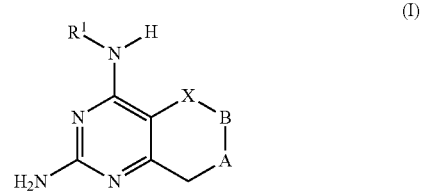

(I)

7 Claims, No Drawings

PIPERIDINO-PYRIMIDINE DERIVATIVES FOR THE TREATMENT OF VIRAL INFECTIONS

This application is a 35 U.S.C. §371 nationalization of PCT application PCT/EP2013/052372, filed Feb. 7, 2013, which claims priority to application EP 12154474.6, filed Feb. 8, 2012 all of which are incorporated herein by reference.

This invention relates to piperdino-pyrimidine derivatives, processes for their preparation, pharmaceutical compositions, and their use in treating viral infections.

The present invention relates to the use of piperidino-pyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081. However, there exists a strong need for novel Toll-Like receptor modulators having preferred selectivity, higher potency, higher metabolic stability, and an improved safety profile (for instance a reduced CVS risk) compared to the compounds of the prior art.

In accordance with the present invention a compound of formula (I) is provided

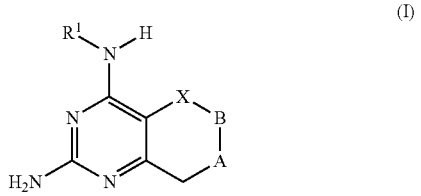

(I)

or a pharmaceutically acceptable salt, tautomer(s), solvate or polymorph thereof, wherein A is selected from the group consisting of $CH_2$, $NCOR^2$, $CHR^3$ and $CR^3R^3$ in any stereo chemical configuration, B is selected from the group consisting of $CH_2$, $NCOR^4$, $CHR^3$ and $CR^3R^3$ in any stereo chemical configuration, with the proviso that when A is $NCOR^2$ then B is not $NCOR^4$ and with the proviso that A and B are not both selected from $CH_2$, $CHR^3$ or $CR^3R^3$, X is selected from $CH_2$ or $CHR^5$ in any stereo chemical configuration, $R^1$ is selected from $C_{1-8}$alkyl optionally substituted with one or more of the following: $C_{1-6}$alkyl, $C_{3-7}$cycloalkyl, hydroxyl, hydroxyalkyl, amino, nitrile, alkoxy, alkoxy($C_{1-4}$)alkyl, carboxylic acid, carboxylic ester, carbamate or sulfone, $R^2$ is selected from substituted and unsubstituted $C_{1-6}$alkyl, $C_{3-7}$cycloalkyl, heterocycle, aryl, heteroaryl, heteroarylalkyl, each of which is optionally substituted by one or more substituents independently selected from halogen, hydroxyl, amino, $C_{1-6}$alkyl, di-($C_{1-6}$)alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl or nitrile, $R^3$ is selected from hydrogen, substituted and unsubstituted $C_{1-6}$alkyl, alkoxy, alkoxy-($C_{1-4}$)alkyl, $C_{3-7}$cycloalkyl, $C_{4-7}$heterocycle, aromatic, bicyclic heterocycle, arylalkyl, heteroaryl, heteroarylalkyl each of which is optionally substituted by one or more substituents independently selected from halogen, hydroxyl, amino, $C_{1-6}$alkyl, di-($C_{1-6}$)alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl or nitrile, $R^4$ is selected from substituted or unsubstituted $C_{1-7}$alkyl, alkoxy, alkoxy-($C_{1-4}$)alkyl, aryl or $C_{3-7}$cycloalkyl each of which is optionally substituted by heterocycle, nitrile, heteroarylalkyl or heteroaryl and wherein $R^5$ is selected from aromatic, bicyclic heterocycle, aryl, heteroaryl, each of which is optionally substituted by one or more substituents independently selected from halogen, hydroxyl, amino, $C_{1-6}$alkyl, di-($C_{1-6}$)alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl or nitrile.

In a first embodiment the present invention provides compounds of formula (I) wherein R1 is butyl and wherein A, B, and X are as specified above.

In a further embodiment the invention concerns compounds of formula (I) wherein $R^1$ is $C_{4-8}$alkyl substituted with hydroxyl, and wherein A, B, and X are as specified above.

Another embodiment relates to compounds of formula I wherein $R^1$, being $C_{4-8}$alkyl substituted with hydroxyl, is one of the following

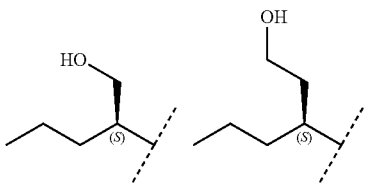

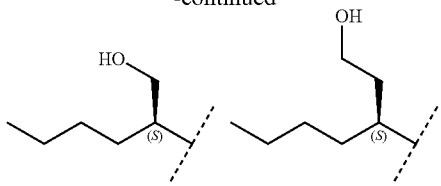

Furthermore, the present invention also provides compounds of formula (I) wherein X is CH$_2$ and wherein A, and B are as specified above.

In another embodiment the present invention provides compounds of formula (I) wherein X is CH$_2$ and wherein A is CH$_2$ and B are as specified above.

Furthermore, the invention relates to compounds of formula (I) wherein R$^2$ is one of the following examples that can be further substituted with C$_{1-3}$alkyl, hydroxyl, alkoxy, nitrile, heterocycle, carboxylic ester, or carboxylic amide:

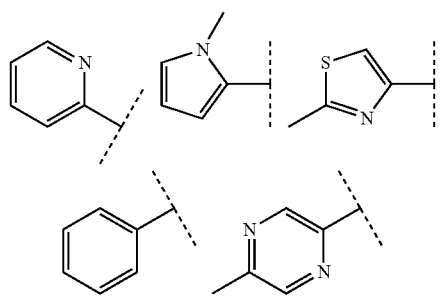

Preferred compounds are compound numbers 3 and 1 having the following chemical structures respectively:

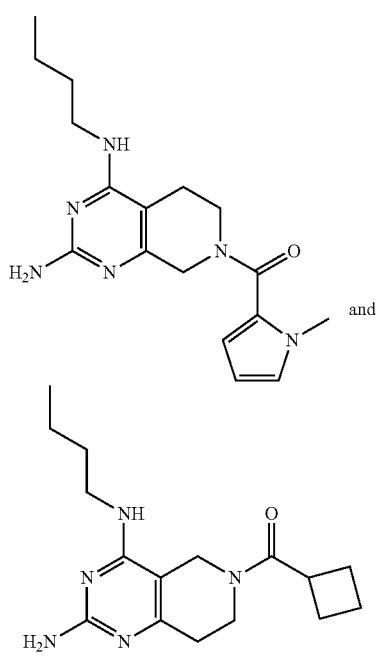

Other preferred compounds according to the invention are the compounds having the following chemical structures:

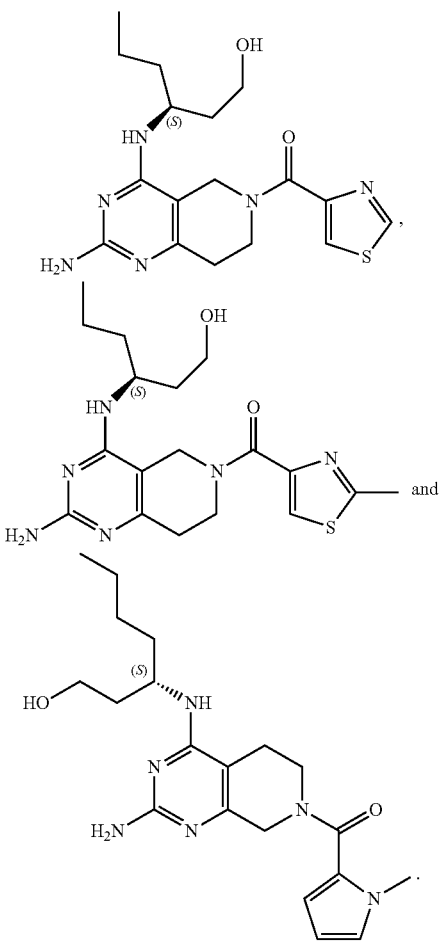

The compounds of formula (I) and their pharmaceutically acceptable salt, tautomer(s), solvate or polymorph thereof have activity as pharmaceuticals, in particular as modulators of Toll-Like Receptors (especially TLR7 and/or TLR8) activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term "alkynyl" refers to an alkyl as defined above consisting of at least two carbon atoms and at least one carbon-carbon triple bond.

The term "cycloalkyl" refers to a carbocyclic ring containing the specified number of carbon atoms.

The term "heteroaryl" means an aromatic ring structure as defined for the term "aryl" comprising at least 1 heteroatom selected from N, O and S, in particular from N and O.

The term "aryl" means an aromatic ring structure optionally comprising one or two heteroatoms selected from N, O and S, in particular from N and O. Said aromatic ring structure may have 4, 5, 6 or 7 ring atoms. In particular, said aromatic ring structure may have 5 or 6 ring atoms.

The term "bicyclic heterocycle" means an aromatic ring structure, as defined for the term "aryl" comprised of two fused aromatic rings. Each ring is optionally comprised of heteroatoms selected from N, O and S, in particular from N and O.

The term "arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

The term "alkoxy" refers to an alkyl (carbon and hydrogen chain) group singular bonded to oxygen like for instance a methoxy group or ethoxy group.

Heterocycle refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Heteroaryl groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, or pyrazinyl.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

General Synthetic Methods

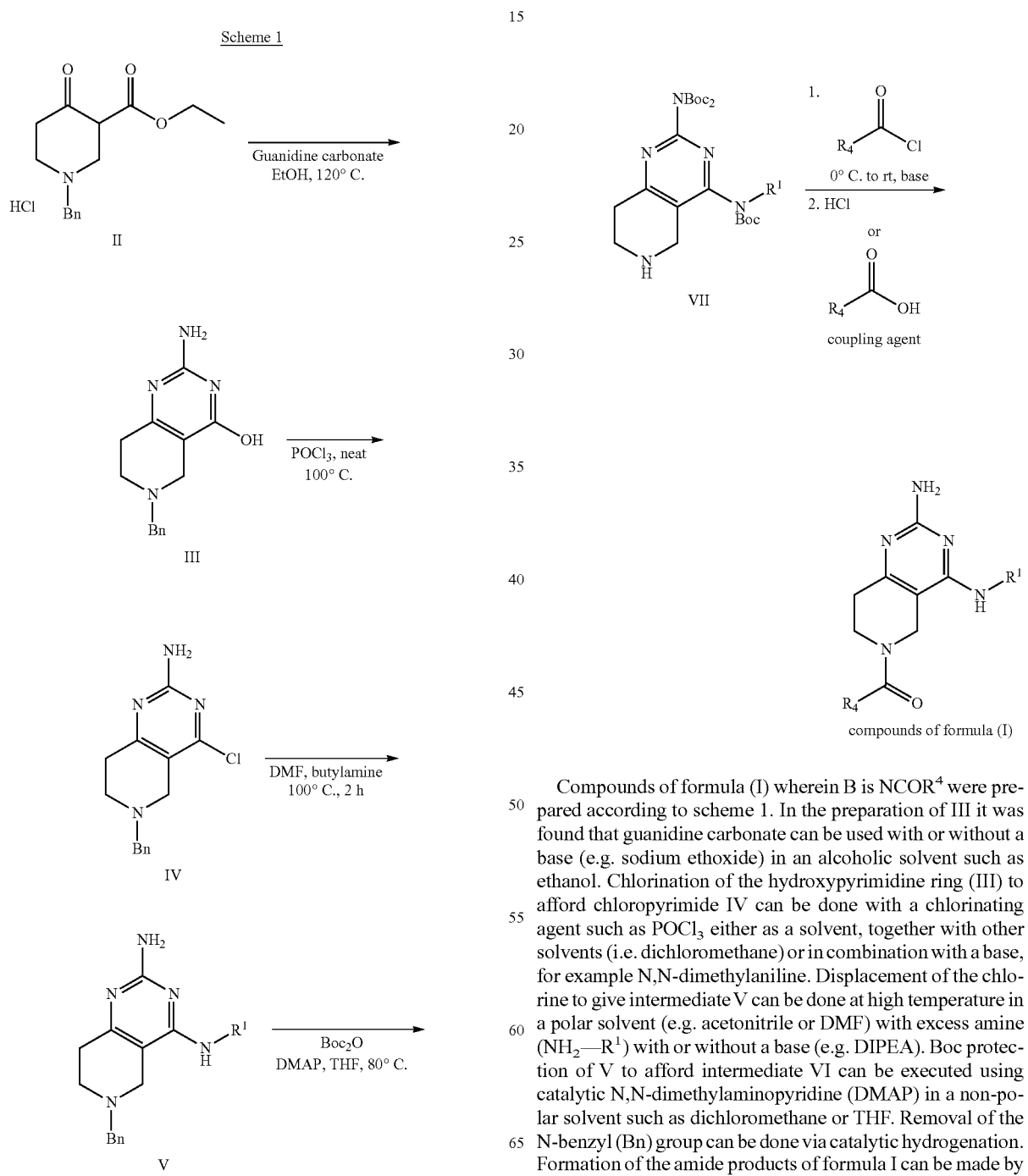

Compounds of formula (I) wherein B is NCOR$^4$ were prepared according to scheme 1. In the preparation of III it was found that guanidine carbonate can be used with or without a base (e.g. sodium ethoxide) in an alcoholic solvent such as ethanol. Chlorination of the hydroxypyrimidine ring (III) to afford chloropyrimide IV can be done with a chlorinating agent such as POCl$_3$ either as a solvent, together with other solvents (i.e. dichloromethane) or in combination with a base, for example N,N-dimethylaniline. Displacement of the chlorine to give intermediate V can be done at high temperature in a polar solvent (e.g. acetonitrile or DMF) with excess amine (NH$_2$—R$^1$) with or without a base (e.g. DIPEA). Boc protection of V to afford intermediate VI can be executed using catalytic N,N-dimethylaminopyridine (DMAP) in a non-polar solvent such as dichloromethane or THF. Removal of the N-benzyl (Bn) group can be done via catalytic hydrogenation. Formation of the amide products of formula I can be made by reacting VII with either: an acid chloride in combination with excess base (e.g. triethylamine); a carboxylic acid in combination with a coupling agent (e.g. HBTU) and a base (e.g. triethylamine).

EXAMPLES

Preparation of Compounds of Formula I

Scheme 2.

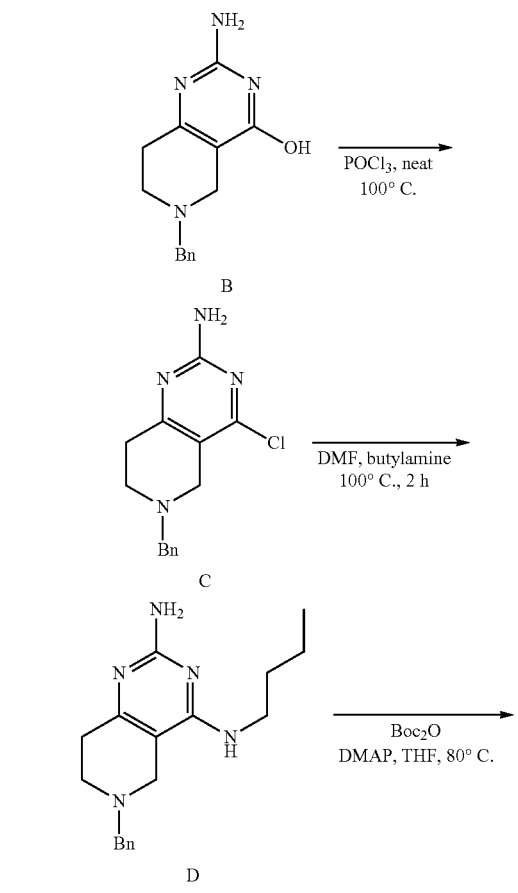

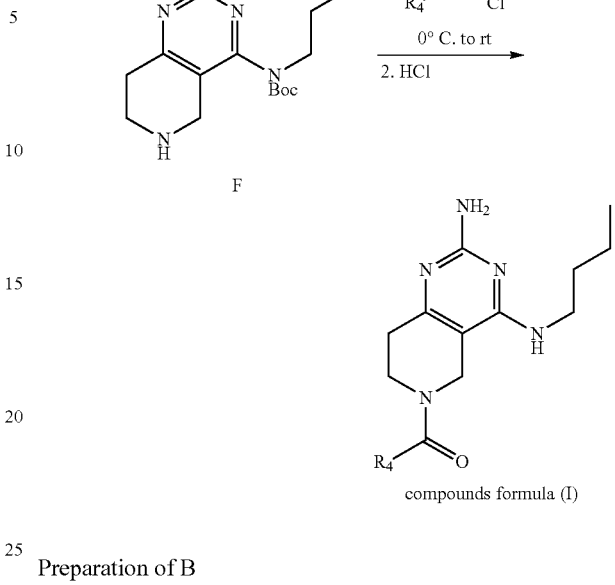

Preparation of B

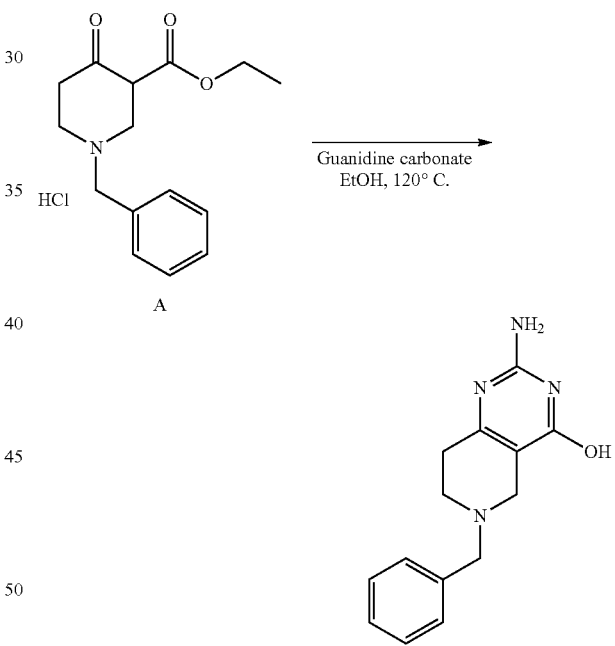

A suspension of A (19.5 g, 68.7 mmol) and guanidine carbonate (19.5 g, 41.23 mmol) in ethanol (170 mL) was heated for 16 hours at 120° C. The solvent was removed under reduced pressure, reconstituted in acetonitril where the crude precipitated and was isolated by filtration. The solid was used as such in the next step without further purification.

1H NMR (300 MHz, DMSO-$d_6$) δ ppm 2.35-2.46 (m, 2H), 2.57-2.65 (m, 2H), 3.04 (s, 2H), 3.60 (s, 2H), 6.28 (br. s., 2H), 7.27 (dt, J=8.7, 4.5 Hz, 1H), 7.31-7.36 (m, 4H), 10.74 (br. s., 1H)

MS m/z: 257 [M+H$^+$]

Preparation of C

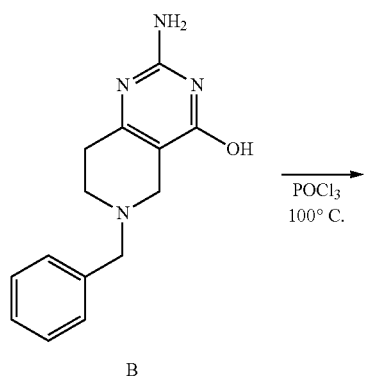

B

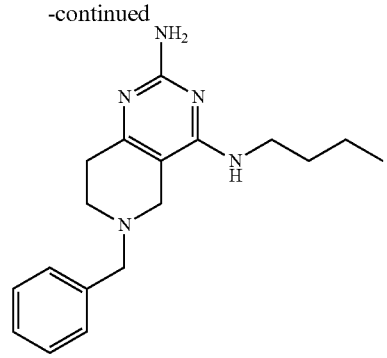

D

A solution of C (2.78 g, 10.12 mmol) in dioxane (25 mL) and n-butylamine (1.5 mL, 15.2 mmol) was heated for 16 hours at 120° C. After cooling to room temperature, the solvent was removed under reduced pressure and the crude was purified via silica gel column chromatography using a dichloromethane to 5% methanol in dichloromethane gradient.

$^1$H NMR (300 MHz, CHLOROFORM-d) δ ppm 0.90-1.01 (m, 3H), 1.28-1.46 (m, 2H), 1.49-1.64 (m, 2H), 2.70-2.81 (m, 4H), 3.21 (s, 2H), 3.44 (td, J=7.1, 5.7 Hz, 2H), 3.74 (s, 2H), 4.47 (br. s., 1H), 5.21-5.46 (m, 2H), 7.30-7.40 (m, 5H)

MS m/z: 312 [M+H$^+$]

Preparation of E

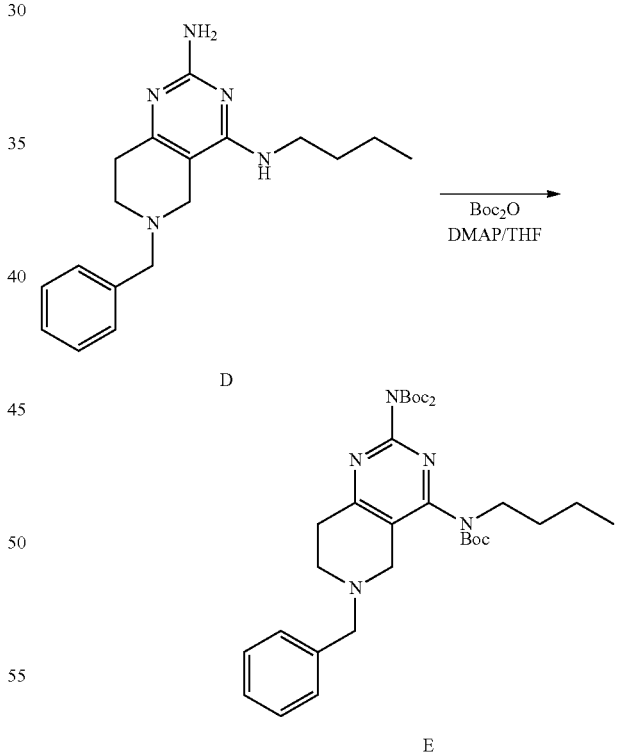

E

A solution of B (8.2 g, 32 mmol) in phosphoryl oxychloride (POCl$_3$) (90 mL) was heated for 16 hours at 100° C. After cooling, the solvent was removed under reduced pressure and the residue was dissolved in ethyl acetate (150 mL), and washed with saturated, aqueous NaHCO$_3$ (3×100 mL). The organic layers were combined, dried over magnesium sulfate, the solids were removed by filtration, and the solvents of the filtrate were removed under reduced pressure. The solid was used in the next step without further purification.

MS m/z: 275 [M+H$^+$]

Preparation of D

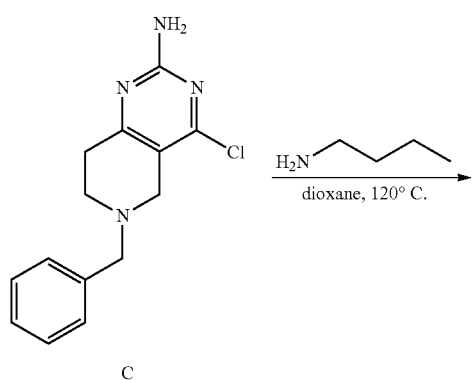

C

A solution of D (3 g, 9.63 mmol), di-tert-butyl dicarbonate (12.6 g, 57.8 mmol) and 4-N,N-dimethylaminopyridine (0.118 g, 0.1 mmol) in THF (60 mL) was heated to 80° C. for 4 hours. The reaction cooled to room temperature and the solvent was removed under reduced pressure. The crude was purified via silica gel column chromatography using a heptane to ethyl acetate gradient.

MS m/z: 612 [M+H$^+$]

Preparation of F

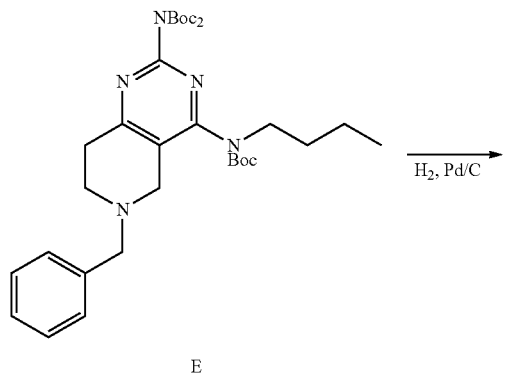

E

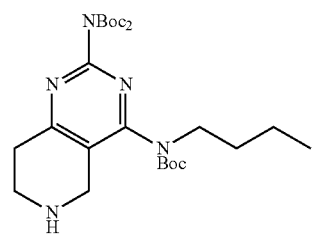

F

To a solution of E (0.711 g, 1.16 mmol) ethanol (6 mL) was added 0.2 w/w equivalent of Pd/C (10%, wet) (71 mg). The flask was sealed; the atmosphere was removed by vacuum. The flask was equipped with a balloon filled with hydrogen gas. The mixture stirs at room temperature for 16 hours. The mixture was filtered over packed celite and the solvent of the filtrate was removed under reduced pressure. The crude was purified via silica gel column chromatography using a dichloromethane to 5% methanol in dichloromethane gradient.

$^1$H NMR (300 MHz, CHLOROFORM-d) δ ppm 0.90 (t, J=7.4 Hz, 3H), 1.19-1.36 (m, 2H), 1.41-1.50 (m, 27H), 1.51-1.58 (m, 2H), 1.64 (s, 2H), 2.91-3.02 (m, 2H), 3.26 (t, J=6.1 Hz, 2H), 3.71-3.82 (m, 2H), 3.86 (s, 1H)

MS m/z: 523 [M+H$^+$]

Preparation of Compound 1

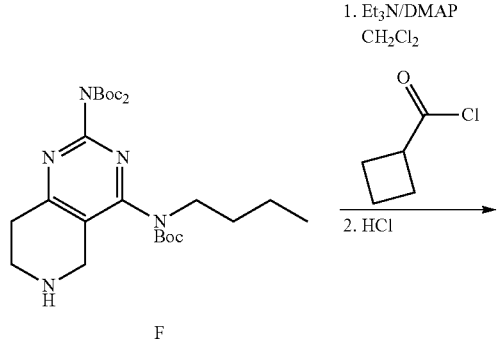

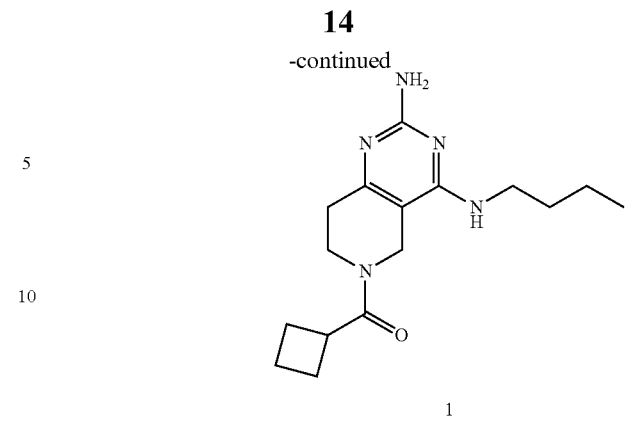

1

To a mixture of F (100 mg, 0.191 mmol), DMAP (2 mg, 0.0.19 mmol) and Et$_3$N (0.081 mL, 0.576 mmol) in dichloromethane (2 mL) was added cyclobutanecarbonyl chloride (25 mg, 0.21 mmol) at 0° C. The mixture was allowed to reach room temperature and stirred for 16 hours. HCl (1N, 1 mL) was added and the reaction stirred for further 30 minutes, then was added NaHCO$_3$ (sat. aq., 10 mL). The mixture was extracted with ethyl acetate (3×10 mL) and the combined organic layers were dried over MgSO$_4$, the solids were removed via filtration and the solvents of the filtrate were removed under reduced pressure. The crude was purified via silica column chromatography using a heptane to ethyl acetate gradient. The best fractions were pooled, and the solvents were removed under reduced pressure to afford compound 1.

MS m/z: 304 [M+H$^+$]

Examples

Compounds of formula (I) wherein A is NCOR$^2$ were prepared according to scheme 3.

Scheme 3.

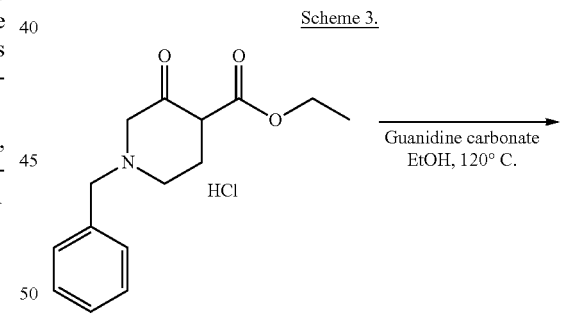

G

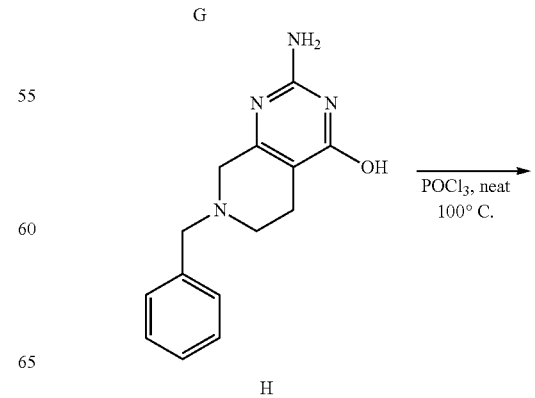

H

-continued

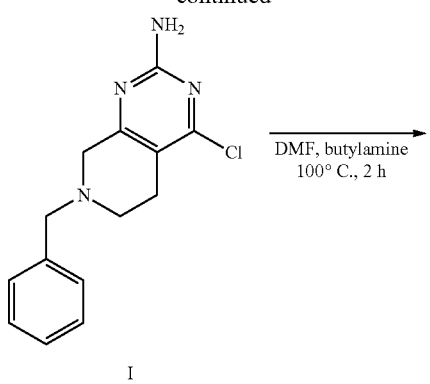

I

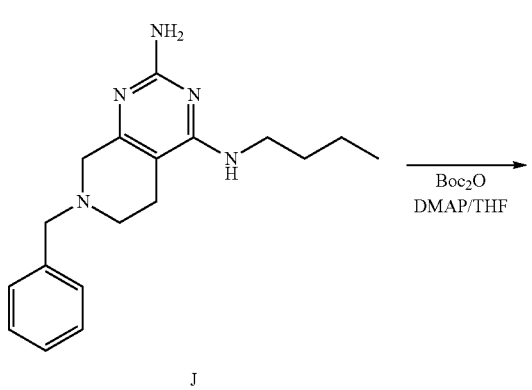

J

K

L

-continued

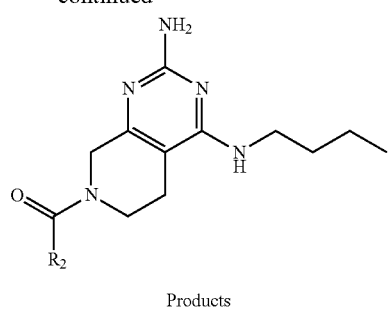

Products

Preparation of H

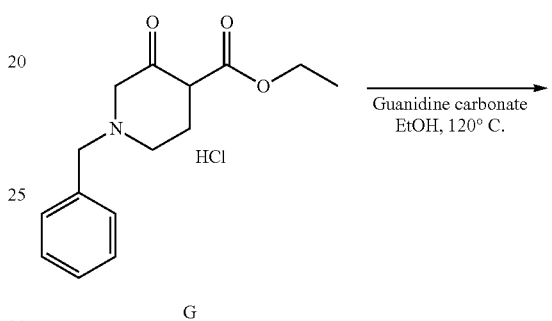

G

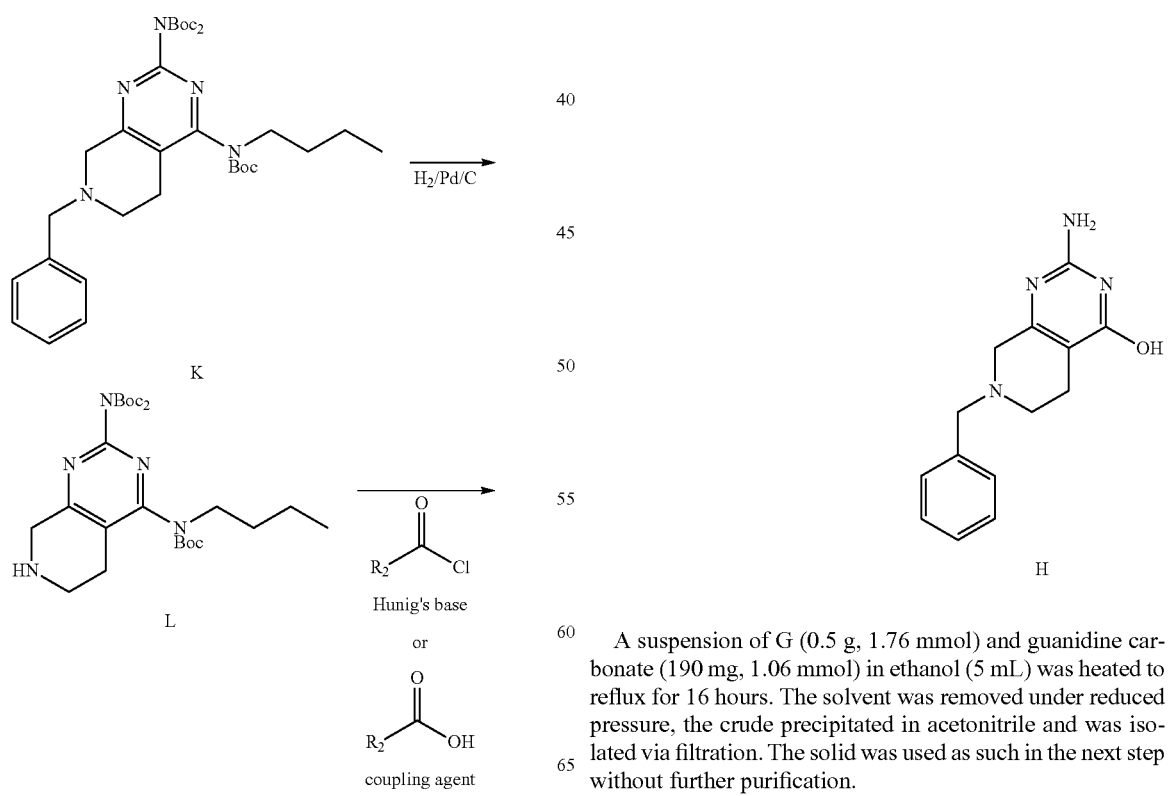

H

A suspension of G (0.5 g, 1.76 mmol) and guanidine carbonate (190 mg, 1.06 mmol) in ethanol (5 mL) was heated to reflux for 16 hours. The solvent was removed under reduced pressure, the crude precipitated in acetonitrile and was isolated via filtration. The solid was used as such in the next step without further purification.

MS m/z: 257 [M+H$^+$]

Preparation of I

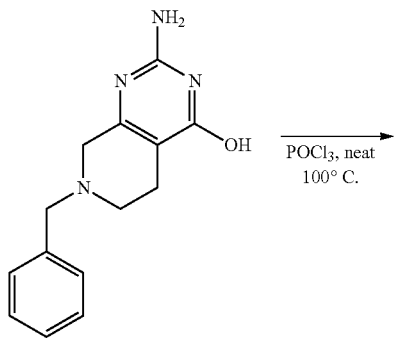

H

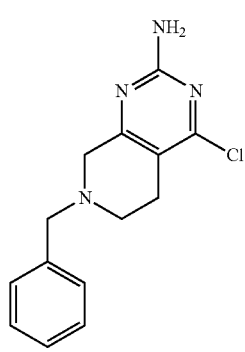

I

A solution of H (6 g, 23.4 mmol) in phosphoryloxychloride (POCl₃) (65 mL) was heated for 3 hours at 100° C. After cooling, the solvent was removed under reduced pressure and the residue was dissolved in ethyl acetate (150 mL), washed with saturated, aqueous NaHCO₃ (3×100 mL). The organic layers were combined, dried over magnesium sulfate, the solids were removed by filtration, and the solvents of the filtrate were removed under reduced pressure. The crude solid was purified via silica gel column chromatography using a dichloromethane in 5% methanol gradient.

MS m/z: 275 [M+H$^+$]

Preparation of J

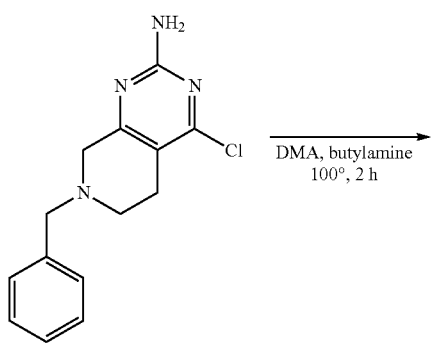

I

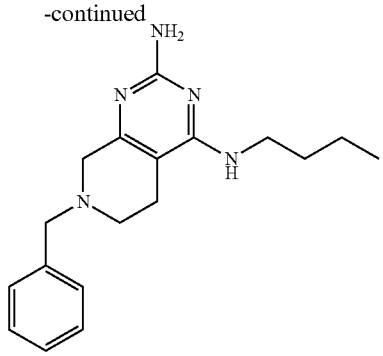

J

A solution of I (2.78 g, 10.12 mmol) in DMA (25 mL) and n-butylamine (1.5 mL, 15.2 mmol) was heated for 16 hours at 120° C. After cooling to room temperature, the solvent was removed under reduced pressure and the crude was purified via silica gel column chromatography using a dichloromethane to 3% methanol in dichloromethane gradient.

$^1$H NMR (300 MHz, CHLOROFORM-d) δ ppm 0.76-0.87 (m, 3H), 1.16-1.35 (m, 2H), 1.38-1.71 (m, 2H), 2.00 (quin, J=6.9 Hz, 2H), 2.64 (td, J=7.4, 2.4 Hz, 2H), 3.46 (dd, J=11.4, 2.6 Hz, 1H), 3.52 (dd, J=5.1, 2.2 Hz, 1H), 3.72 (s, 2H), 3.84 (td, J=6.3, 1.8 Hz, 1H), 4.06 (d, J=2.7 Hz, 1H), 4.48 (br. s., 2H), 4.89 (d, J=8.7 Hz, 1H), 6.72-6.80 (m, 2H), 7.02 (d, J=8.7 Hz, 2H), 7.25 (s, 1H)

MS m/z: 312 [M+H$^+$]

Preparation of K

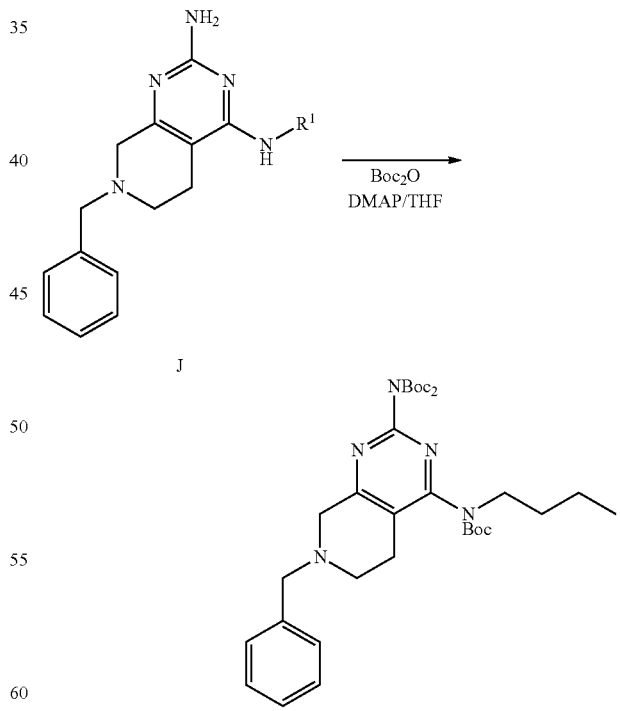

A solution of J (3 g, 9.63 mmol), di-tert-butyl dicarbonate (12.6 g, 57.8 mmol) and 4-N,N-dimethylamino pyridine (0.118 g, 0.1 mmol) in THF (50 mL) was heated to 80° C. for 4 hours. The reaction cooled to room temperature and the solvent was removed under reduced pressure. The crude was purified via silica gel column chromatography using a heptane to ethyl acetate gradient.

MS m/z: 612 [M+H⁺]

Preparation of L

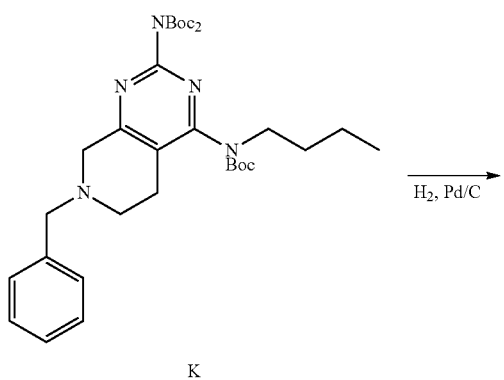

K

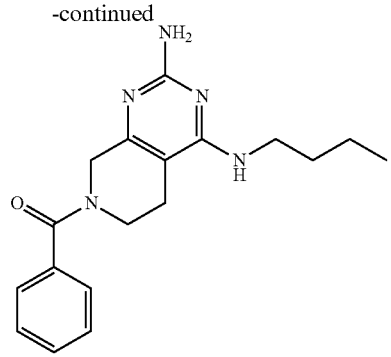

-continued

2

To a solution of L (100 mg, 0.191 mmol) was added Et₃N (58 mg, 0.58 mmol) benzoyl chloride (30 mg, 0.211 mmol) in dichloromethane (3 mL), and DMAP (2 mg, 0.019 mmol) then stirred at room temperature for 16 hours. To this was added NaHCO₃ (sat., aq., 10 mL) and the mixture was extracted with ethyl acetate (3×10 mL). The organic layers were combined, dried over MgSO₄, the solids were removed via filtration and the solvents of the filtrate were removed under reduced pressure. The crude was purified via silica column chromatography using a dichloromethane to 5% methanol in dichloromethane gradient. The purified boc-protected product was deprotected by addition of HCl in isopropanol.

Preparation of Compound 3

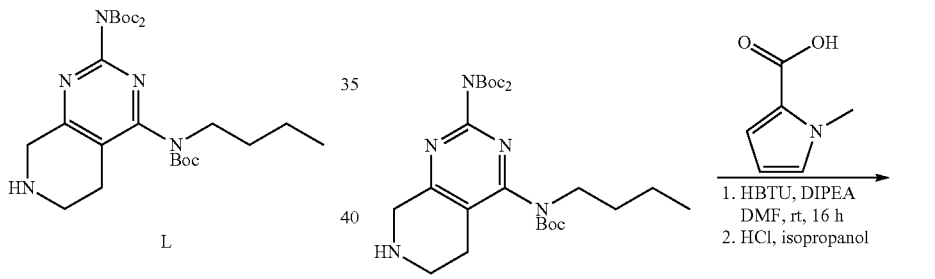

L

To a solution of K (0.711 g. 1.16 mmol) ethanol (6 mL) was added 0.2 w/w equivalent of Pd/C (10%, wet) (0.071 g) and stirred under an atmosphere of hydrogen (balloon) for 16 hours. The mixture was filtered over packed celite and the solvent of the filtrate was removed under reduced pressure. The crude was purified via silica gel column chromatography using a heptanes to ethyl acetate gradient.

MS m/z: 523 [M+H⁺]

Preparation of Compound 2

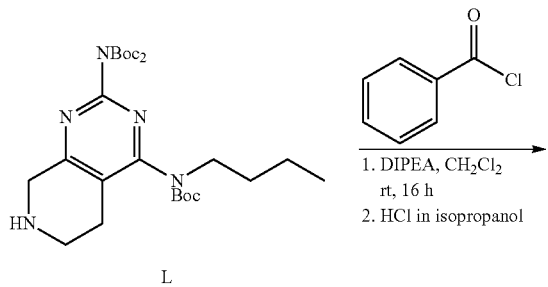

L

3

To a solution of L (90 mg, 0.173 mmol) in DMF (3 mL) was added DIPEA (33 mg, 0.26 mmol), HBTU (72 mg, 0.19 mmol) and 1-methyl-2-pyrrolecarboxylic acid (23 mg, 0.18 mmol) was added then stirred at room temperature for 16 hours. To this was added NaHCO₃ (sat., aq., 10 mL) and the mixture was extracted with ethyl acetate (3×10 mL). The organic layers were combined, dried (MgSO₄), the solids were removed by filtration and the solvents of the filtrate were removed under reduced pressure. The crude was purified via silica column chromatography using a using a dichloromethane to 3% methanol in dichloromethane gradient. The purified boc-protected product was deprotected by addition of HCl in isopropanol.

Preparation of Compound 4

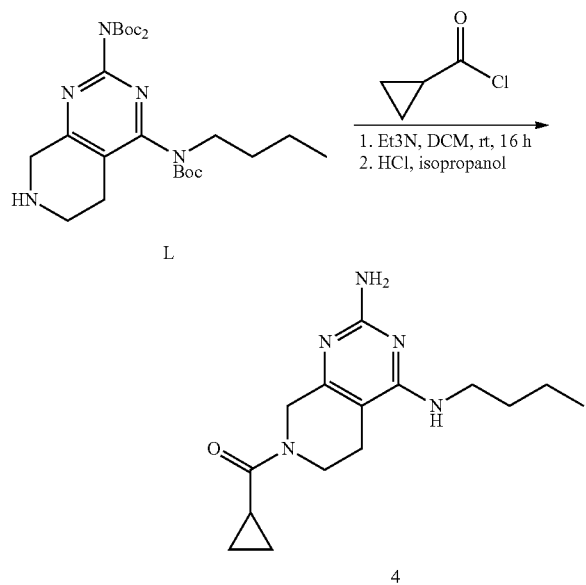

To a stirring solution of L (110 mg, 0.2 mmol) in dichloromethane (2 mL), triethylamine (60 mg, 0.6 mmol), DMAP (6 mg, 0.05 mmol) and cyclopropanecarbonyl chloride (24 mg, 0.23 mmol) were added and the mixture stirred at room temperature for 16 hours. To this was added $NaHCO_3$ (sat., aq., 50 mL) and the mixture was extracted with ethyl acetate (3×10 mL). The organic layers were combined, dried ($MgSO_4$), the solids were removed by filtration and the solvents of the filtrate were removed under reduced pressure. The crude was purified via silica column chromatography using a heptane to ethyl acetate gradient. The purified boc-protected product was deprotected by addition of HCl in isopropanol.

Table 1: Compounds of Formula (I).

Products were prepared by one of the methods described above.

Table I A represent compounds wherein $A=NCOR^2$ while Table I B represents compounds wherein $B=NCOR^4$ and Table I C contains both region-isomeric compounds respectively.

TABLE I A

| # | STRUCTURE | Exact Mass | LC-MS (M + H) | NMR |
|---|---|---|---|---|
| 2 | 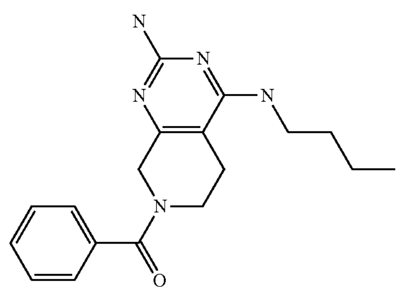 [SMILES: CCCCNc1nc(N)nc2c1CCN(C(=O)c1ccccc1)C2] | 325.19 | 326 | 1H NMR (300 MHz, CHLOROFORM-d) δ ppm 0.89 (t, J = 7.3 Hz, 3 H), 1.25-1.40 (m, 2 H), 1.51 (quin, J = 7.3 Hz, 2 H), 1.59 (s, 1 H), 2.34 (br. s., 2 H), 3.37 (td, J = 7.0, 5.7 Hz, 2 H), 3.95 (br. s., 1 H), 4.12-4.72 (m, 5 H), 7.35 (d, J = 2.7 Hz, 5 H) |
| 3 | 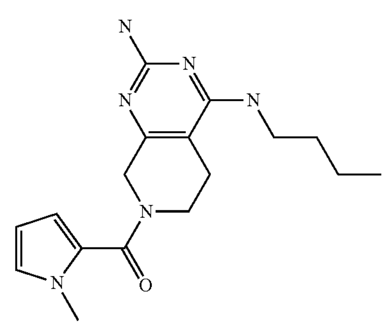 [SMILES: CCCCNc1nc(N)nc2c1CCN(C(=O)c1cccn1C)C2] | 328.20 | 329 | 1H NMR (300 MHz, METHANOL-d4) δ ppm 0.86 (t, J = 7.4 Hz, 3 H), 1.29 (dd, J = 15.1, 7.4 Hz, 2 H), 1.41-1.57 (m, 2 H), 2.34 (s, 2 H), 3.31 (t, J = 7.2 Hz, 2 H), 3.63 (s, 3 H), 3.85 (t, J = 6.0 Hz, 2 H), 4.42 (s, 3 H), 4.51-4.62 (m, 2 H), 6.01 (dd, J = 3.8, 2.6 Hz, 1 H), 6.37 (dd, J = 3.8, 1.6 Hz, 1 H), 6.74 (d, J = 2.2 Hz, 1 H) |

TABLE I A-continued

| # | STRUCTURE | Exact Mass | LC-MS (M + H) | NMR |
|---|---|---|---|---|
| 4 | 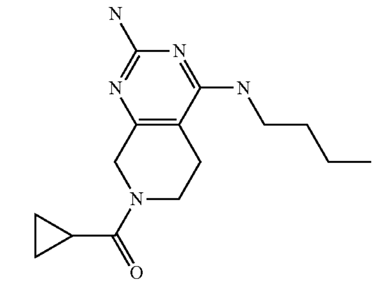 [SMILES: CCCCNc1nc(N)nc2c1CCN(C(=O)C1CC1)C2] | 289.19 | 290 | 1H NMR (300 MHz, CHLOROFORM-d) δ ppm 0.73-0.84 (m, 2 H), 0.92-0.99 (m, 3 H), 1.00 (br. s., 1 H), 1.40 (dq, J = 14.9, 7.3 Hz, 2 H), 1.59 (quin, J = 7.3 Hz, 2 H), 1.70 (s, 3 H), 1.78 (br. s., 1 H), 2.25-2.48 (m, 2 H), 3.36-3.51 (m, 2 H), 3.88 (m, J = 5.1 Hz, 2 H), 4.39-4.57 (m, 2 H), 4.63 (br. s., 1 H) |
| 9 | 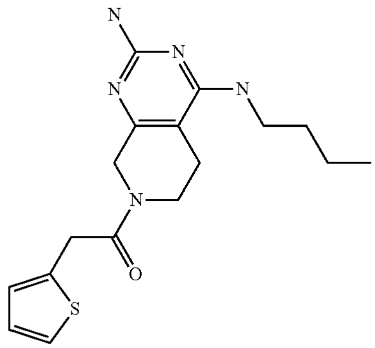 [SMILES: CCCCNc1nc(N)nc2c1CCN(C(=O)Cc1cccs1)C2] | 345.16 | 346 | 1H NMR (300 MHz, DMSO-d6) δ ppm 0.92 (t, J = 7.3 Hz, 3 H), 1.24-1.42 (m, 2 H), 1.49-1.63 (m, 2 H), 2.31 (s, 2 H), 3.26-3.41 (m, 2 H), 3.74 (s, 2 H), 4.00 (s, 2 H), 4.26 (s, 2 H), 5.39 (br. s., 2 H), 5.93-6.10 (m, 1 H), 6.85-7.01 (m, 2 H), 7.27-7.40 (m, 1 H) |
| 10 | 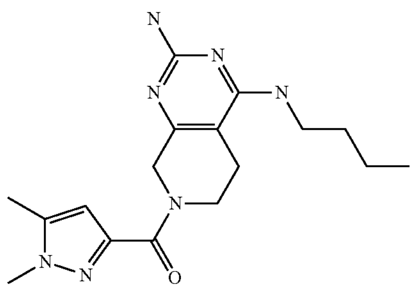 [SMILES: CCCCNc1nc(N)nc2c1CCN(C(=O)c1cc(C)n(C)n1)C2] | 343.21 | 344 | 1H NMR (300 MHz, METHANOL-d4) δ ppm 0.85 (t, J = 7.3 Hz, 4 H), 1.28 (d, J = 7.8 Hz, 3 H), 1.49 (t, J = 7.3 Hz, 3 H), 2.15 (s, 3 H), 2.29-2.39 (m, 2 H), 3.33 (t, J = 7.2 Hz, 2 H), 3.73 (s, 4 H), 3.81-3.96 (m, 1 H), 4.22-4.51 (m, 2 H), 6.22 (s, 1 H) |
| 11 | 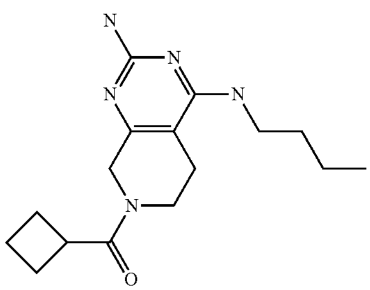 [SMILES: CCCCNc1nc(N)nc2c1CCN(C(=O)C1CCC1)C2] | 303.21 | 304 | 1H NMR (300 MHz, DMSO-d6) δ ppm 0.85-1.00 (m, 3 H), 1.24-1.43 (m, 3 H), 1.50-1.61 (m, 2 H), 1.74-1.87 (m, 1 H), 1.92-2.03 (m, 1 H), 2.09-2.23 (m, 3 H), 2.27-2.34 (m, 2 H), 3.28-3.47 (m, 3 H), 3.54-3.69 (m, 2 H), 4.05-4.23 (m, 2 H), 5.31-5.47 (m, 2 H), 5.92-6.07 (m, 1 H) |
| 12 | 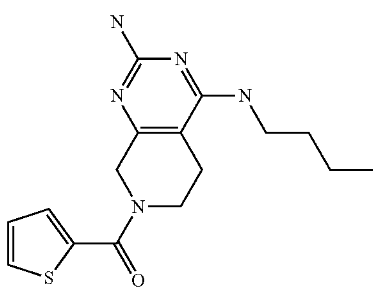 [SMILES: CCCCNc1nc(N)nc2c1CCN(C(=O)c1cccs1)C2] | 331.15 | 332 | 1H NMR (300 MHz, DMSO-d6) δ ppm 0.90 (t, J = 1.0 Hz, 3 H), 1.21-1.38 (m, 2 H), 1.45-1.58 (m, 2 H), 2.33-2.43 (m, 2 H), 3.23-3.32 (m, 2 H), 3.75-3.89 (m, 2 H), 4.31-4.46 (m, 2 H), 5.67-5.83 (m, 2 H), 6.31-6.47 (m, 1 H), 7.08-7.23 (m, 1 H), 7.40-7.52 (m, 1 H), 7.75-7.84 (m, 1 H) |

TABLE I A-continued

| # | STRUCTURE | Exact Mass | LC-MS (M + H) | NMR |
|---|---|---|---|---|
| 13 | 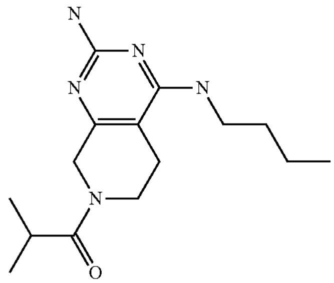 [SMILES: CCCCNc1nc(N)nc2c1CCN(C(=O)C(C)C)C2] | 291.21 | 292 | 1H NMR (300 MHz, DMSO-d6) δ ppm 0.84 (t, J = 7.3 Hz, 3 H), 0.96 (d, J = 6.7 Hz, 6 H), 1.26 (d, J = 7.4 Hz, 2 H), 1.46 (t, J = 7.2 Hz, 2 H), 2.25 (br. s., 2 H), 2.75-2.89 (m, 1 H), 3.26 (d, J = 6.6 Hz, 2 H), 3.62 (t, J = 5.8 Hz, 2 H), 4.15 (s, 2 H), 5.29 (br. s., 2 H), 5.82-6.04 (m, 1 H), |
| 14 | 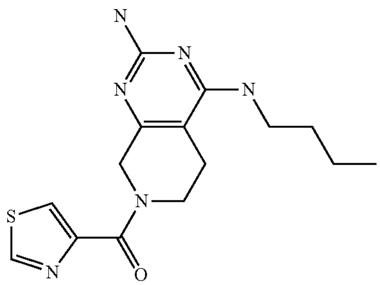 [SMILES: CCCCNc1nc(N)nc2c1CCN(C(=O)c1cscn1)C2] | 332.14 | 333 | 1H NMR (300 MHz, METHANOL-d4) δ ppm 0.86 (t, J = 7.3 Hz, 3 H), 1.28 (m, J = 7.8 Hz, 2 H), 1.50 (s, 2 H), 2.31-2.49 (m, 2 H), 3.29-3.40 (m, 2 H), 3.91 (t, J = 5.8 Hz, 2 H), 4.39-4.63 (m, 2 H), 8.05 (d, J = 1.9 Hz, 1 H), 8.97 (d, J = 2.1 Hz, 1 H) exchangable protons not shown. |
| 15 | 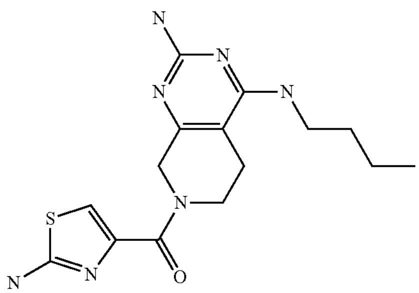 [SMILES: CCCCNc1nc(N)nc2c1CCN(C(=O)c1csc(N)n1)C2] | 347.15 | 348 | 1H NMR (300 MHz, DMSO-d6) δ ppm 0.92 (t, J = 7.3 Hz, 3 H), 1.35 (d, J = 7.3 Hz, 2 H), 1.55 (s, 2 H), 2.36 (s, 2 H), 3.34 (d, J = 6.5 Hz, 2 H), 3.86 (s, 2 H), 4.42 (s, 2 H), 5.36 (s, 2 H), 5.90-6.06 (m, 1 H), 6.82 (br. s., 2 H), 6.97 (s, 1 H) |
| 16 | 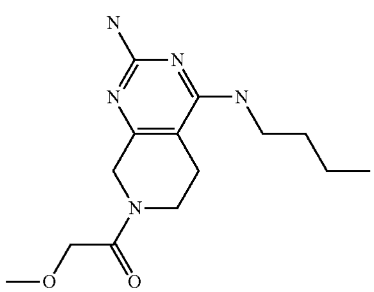 [SMILES: CCCCNc1nc(N)nc2c1CCN(C(=O)COC)C2] | 293.19 | 294 | 1H NMR (300 MHz, DMSO-d6) δ ppm 0.84 (t, J = 1.0 Hz, 3 H), 1.16-1.20 (m, 1 H), 1.22-1.34 (m, 2 H), 1.39-1.55 (m, 2 H), 2.18-2.33 (m, 2 H), 3.24 (s, 4 H), 3.52-3.65 (m, 2 H), 4.04 (s, 2 H), 4.12 (s, 2 H), 5.20-5.39 (m, 2 H), 5.85-6.01 (m, 1 H) |
| 17 | 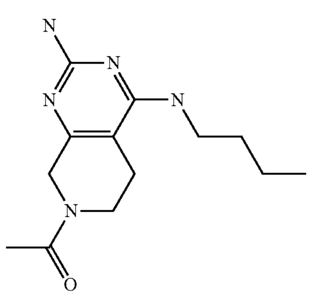 [SMILES: CCCCNc1nc(N)nc2c1CCN(C(C)=O)C2] | 263.17 | 264 | 1H NMR (300 MHz, CHLOROFORM-d) δ ppm 0.97 (t, J = 7.3 Hz, 3 H), 1.36-1.47 (m, 2 H), 1.52-1.61 (m, 2 H), 2.12-2.20 (m, 3 H), 2.26-2.42 (m, 2 H), 3.35-3.52 (m, 2 H), 3.70 (t, J = 5.8 Hz, 1 H), 3.86 (t, J = 5.9 Hz, 1 H), 4.31 (s, 2 H), 4.40-4.50 (m, 1 H), 4.65 (br. s., 2 H) |

TABLE I A-continued

| # | STRUCTURE | Exact Mass | LC-MS (M + H) | NMR |
|---|-----------|-----------|---------------|-----|
| 18 | 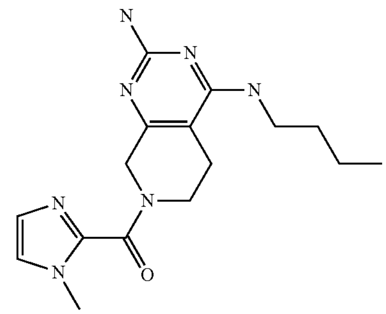 [SMILES: CCCCNc1nc(N)nc2c1CCN(C(=O)c1nccn1C)C2] | 329.20 | 330 | 1H NMR (300 MHz, METHANOL-d4) δ ppm 0.86 (t, J = 7.4 Hz, 3 H), 1.28 (m, J = 15.2, 7.4 Hz, 2 H), 1.51 (m, J = 7.2, 7.2 Hz, 2 H), 2.32-2.51 (m, 2 H), 3.38 (t, J = 7.2 Hz, 2 H), 3.73 (s, 3 H), 3.91 (d, J = 5.4 Hz, 2 H), 4.40-4.54 (m, 1 H), 4.67 (br. s., 1 H), 6.96 (s, 1 H), 7.14 (s, 1 H) exchangable protons not shown. |
| 19 | 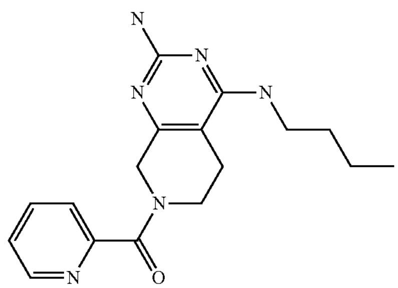 [SMILES: CCCCNc1nc(N)nc2c1CCN(C(=O)c1ccccn1)C2] | 326.19 | 327 | 1H NMR (300 MHz, DMSO-d6) δ ppm 0.92 (t, J = 7.3 Hz, 3 H), 1.30-1.43 (m, 2 H), 1.55 (m, J = 7.1, 7.1 Hz, 2 H), 2.40 (t, J = 5.5 Hz, 2 H), 3.35 (m, J = 6.5 Hz, 2 H), 3.51-3.98 (m, 2 H), 4.23-4.45 (m, 2 H), 5.40 (br. s., 2 H), 5.94-6.14 (m, 1 H), 7.42-7.52 (m, 1 H), 7.60 (d, J = 7.8 Hz, 1 H), 7.83-8.00 (m, 1 H), 8.61 (d, J = 4.7 Hz, 1H) |
| 20 | 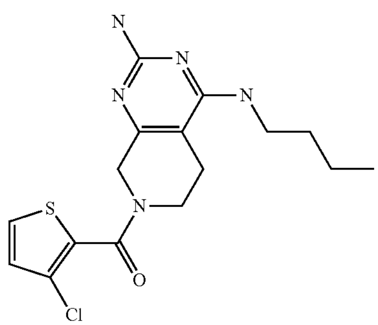 [SMILES: CCCCNc1nc(N)nc2c1CCN(C(=O)c1sccc1Cl)C2] | 365.11 | 366 | 1H NMR (300 MHz, CHLOROFORM-d) δ ppm 0.97 (t, J = 7.3 Hz, 3 H), 1.40 (dq, J = 14.9, 7.3 Hz, 2 H), 1.51-1.67 (m, 2 H), 2.44 (t, J = 5.8 Hz, 2 H), 3.45 (td, J = 7.1, 5.6 Hz, 2 H), 3.79-4.11 (m, 2 H), 4.34-4.55 (m, 3 H), 4.66 (br. s., 2 H), 6.92 (d, J = 5.2 Hz, 1 H), 7.38 (d, J = 5.2 Hz, 1 H) |
| 21 | 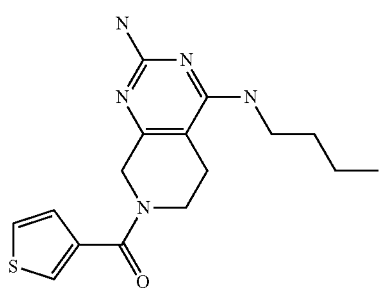 [SMILES: CCCCNc1nc(N)nc2c1CCN(C(=O)c1ccsc1)C2] | 331.15 | 332 | 1H NMR (300 MHz, CHLOROFORM-d) δ ppm 0.96 (t, J = 7.3 Hz, 3 H), 1.34-1.48 (m, 2 H), 1.51-1.66 (m, 2 H), 1.98 (br. s., 2 H), 2.41 (t, J = 5.7 Hz, 2 H), 3.36-3.51 (m, 2 H), 3.76-4.11 (m, 2 H), 4.49 (br. s., 2 H), 4.66 (br. s., 1 H), 7.23 (dd, J = 4.9, 1.1 Hz, 1 H), 7.34 (dd, J = 4.9, 3.0 Hz, 1 H), 7.58 (dd, J = 2.9, 1.2 Hz, 1 H) |
| 22 | 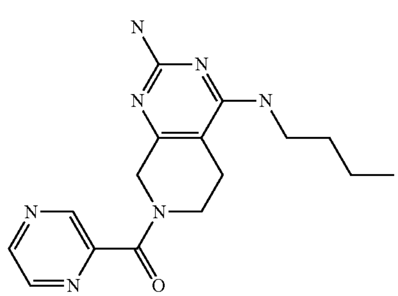 [SMILES: CCCCNc1nc(N)nc2c1CCN(C(=O)c1cnccn1)C2] | 327.18 | 328 | 1H NMR (300 MHz, CHLOROFORM-d) δ ppm 0.96 (t, J = 7.3 Hz, 3 H), 1.40 (dq, J = 15.0, 7.3 Hz, 2 H), 1.52-1.67 (m, 2 H), 1.88 (br. s., 2 H), 2.49 (q, J = 6.0 Hz, 2 H), 3.35-3.51 (m, 2 H), 4.07 (t, J = 5.9 Hz, 1 H), 4.51-4.69 (m, 3 H), 4.77 (br. s., 1 H), 8.57 (m, J = 2.2, 1.4 Hz, 1 H), 8.62-8.70 (m, 1 H), 8.96-9.05 (m, 1 H) |

TABLE I A-continued

| # | STRUCTURE | Exact Mass | LC-MS (M + H) | NMR |
|---|---|---|---|---|
| 23 | 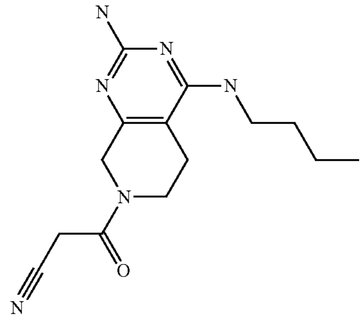 [SMILES: CCCCNc1nc(N)nc2c1CCN(C(=O)CC#N)C2] | 288.17 | 289 | 1H NMR (300 MHz, DMSO-d6) δ ppm 0.89 (t, J = 7.3 Hz, 3 H), 1.30 (dq, J = 14.9, 7.3 Hz, 2 H), 1.50 (quin, J = 7.3 Hz, 2 H), 2.26 (t, J = 5.6 Hz, 1 H), 2.36 (t, J = 5.6 Hz, 1 H), 3.24-3.33 (m, 2 H), 3.57 (t, J = 5.8 Hz, 1 H), 3.67 (t, J = 5.7 Hz, 1 H), 4.11 (s, 1 H), 4.13 (s, 2 H), 4.19 (s, 1 H), 5.76 (d, J = 7.3 Hz, 2 H), 6.40 (t, J = 5.4 Hz, 1 H) |
| 24 | 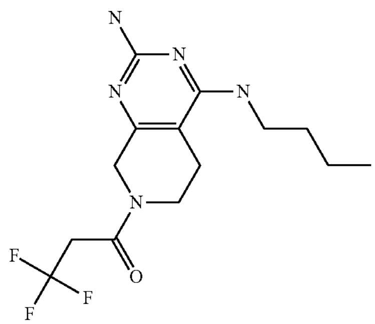 [SMILES: CCCCNc1nc(N)nc2c1CCN(C(=O)CC(F)(F)F)C2] | 331.16 | 332 | 1H NMR (300 MHz, CHLOROFORM-d) δ ppm 0.96 (t, J = 7.3 Hz, 3 H), 1.40 (dq, J = 15.0, 7.2 Hz, 2 H), 1.59 (quin, J = 7.3 Hz, 2 H), 1.85 (br. s., 2 H), 2.34 (t, J = 5.9 Hz, 1 H), 2.41 (t, J = 5.8 Hz, 1 H), 3.20-3.37 (m, 2 H), 3.45 (td, J = 7.0, 5.7 Hz, 2 H), 3.73 (t, J = 5.8 Hz, 1 H), 3.91 (t, J = 5.9 Hz, 1 H), 4.31 (s, 1H), 4.58-4.81 (m, 2 H) |

TABLE I B

| # | STRUCTURE | Exact Mass | LC-MS (M + H) | NMR |
|---|---|---|---|---|
| 1 | 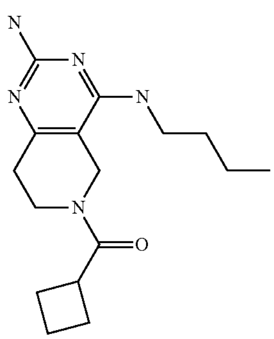 [SMILES: CCCCNc1nc(N)nc2c1CN(C(=O)C1CCC1)CC2] | 303.21 | 304 | 1H NMR (300 MHz, DMSO-d6) δ ppm 0.94 (t, J = 1.0 Hz, 3 H), 1.29-1.43 (m, 2 H), 1.51-1.64 (m, 2 H), 1.73-1.84 (m, 1 H), 1.90-2.02 (m, 1 H), 2.08-2.29 (m, 4 H), 2.39-2.47 (m, 1 H), 3.19-3.25 (m, 1 H), 3.29-3.48 (m, 3 H), 3.52-3.63 (m, 2 H), 4.05-4.27 (m, 2 H), 5.33-5.49 (m, 2 H), 6.03-6.23 (m, 1 H) |
| 5 | 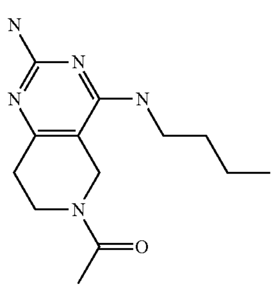 [SMILES: CCCCNc1nc(N)nc2c1CN(C(C)=O)CC2] | 263.17 | 264 | 1H NMR (300 MHz, CHLOROFORM-d) δ ppm 0.90-0.98 (m, 3 H), 1.39 (dq, J = 14.9, 7.3 Hz, 2 H), 1.50-1.65 (m, 2 H), 2.19 (s, 3 H), 2.69 (t, J = 5.8 Hz, 2 H), 3.43 (td, J = 7.1, 5.6 Hz, 2 H), 3.68 (t, J = 5.9 Hz, 2 H), 4.29 (s, 2 H), 4.46-4.57 (m, 1 H), 4.67-4.85 (m, 2 H) |

TABLE I B-continued

| # | STRUCTURE | Exact Mass | LC-MS (M + H) | NMR |
|---|---|---|---|---|
| 6 | 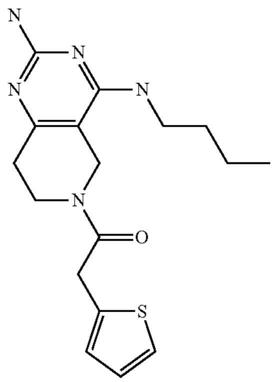 [SMILES: CCCCNc1nc(N)nc2c1CN(C(=O)Cc1cccs1)CC2] | 345.16 | 346 | 1H NMR (300 MHz, DMSO-d6) δ ppm 0.90 (m, J = 6.6 Hz, 3 H), 1.18-1.37 (m, 2 H), 1.44-1.59 (m, 2 H), 2.32-2.40 (m, 2 H), 3.21-3.29 (m, 2 H), 3.61-3.76 (m, 2 H), 4.03 (s, 2 H), 4.16-4.34 (m, 2 H), 5.61-5.78 (m, 2 H), 6.24-6.45 (m, 1 H), 6.85-7.03 (m, 2 H), 7.30-7.46 (m, 1 H) |
| 7 | 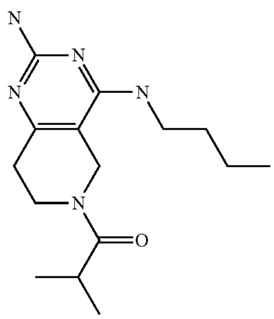 [SMILES: CCCCNc1nc(N)nc2c1CN(C(=O)C(C)C)CC2] | 291.21 | 292 | 1H NMR (300 MHz, DMSO-d6) δ ppm 0.75 (t, J = 7.4 Hz, 3 H), 0.87 (d, J = 6.7 Hz, 6 H), 1.19 (s, 2 H), 1.38 (s, 2 H), 2.24-2.30 (m, 2 H), 2.74-2.77 (m, 1 H), 3.18 (d, J = 6.6 Hz, 2 H), 3.50 (s, 2 H), 4.06 (s, 2 H), 5.18 (br. s., 2 H), 5.86-6.02 (m, 1 H) |
| 8 | 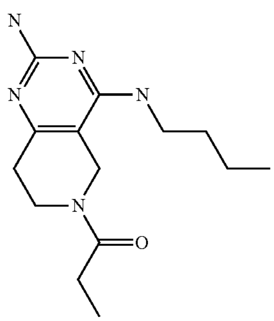 [SMILES: CCCCNc1nc(N)nc2c1CN(C(=O)CC)CC2] | 277.19 | 278 | 1H NMR (300 MHz, DMSO-d6) δ ppm 0.96 (td, J = 7.3, 3.6 Hz, 3 H), 1.07 (t, J = 7.4 Hz, 3 H), 1.37 (s, 2 H), 1.56 (br. s., 2 H), 2.45 (dd, J = 7.4, 3.0 Hz, 3 H), 2.50-2.54 (m, 1 H), 3.29-3.34 (m, 2 H), 3.68 (d, J = 8.0 Hz, 2 H), 4.23 (d, J = 7.6 Hz, 2 H), 4.31-4.31 (m, 0 H), 5.80 (d, J = 8.2 Hz, 2 H), 6.34-6.57 (m, 1 H) |

TABLE I C

| # | STRUCTURE | Exact Mass | LC-MS (M + H) | NMR |
|---|---|---|---|---|
| 25 | 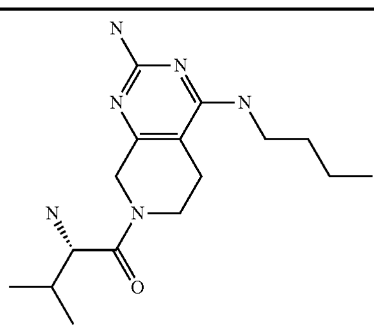 | 320.2 | 321 | 1H NMR (300 MHz, CHLOROFORM-d) δ ppm 0.68-1.01 (m, 7 H), 1.32 (dq, J = 14.9, 7.3 Hz, 2 H), 1.43-1.62 (m, 6H), 1.76 (dd, J = 12.5, 6.3 Hz, 1 H), 2.26 (td, J = 14.2, 6.1 Hz, 2 H), 3.36 (q, J = 6.6 Hz, 2 H), 3.42 (s, 1 H), 3.49 (d, J = 5.2 Hz, 1 H), 3.66 (br. s., 1H), 3.71-3.95 (m, 1 H), 4.17-4.30 (m, 1 H), 4.32-4.46 (m, 1 H), 4.53 (br. s., 2 H) |

TABLE I C-continued

| # | STRUCTURE | Exact Mass | LC-MS (M + H) | NMR |
|---|---|---|---|---|
| 26 | 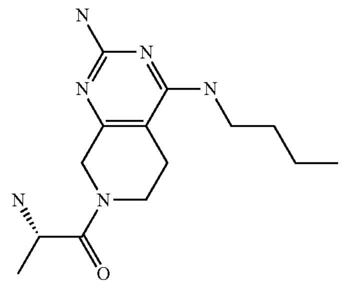 [SMILES: CCCCNc1nc(N)nc2c1CCN(C(=O)[C@H](C)N)C2] | 292.2 | 293 | ¹H NMR (300 MHz, CHLOROFORM-d) δ ppm 0.89 (t, J = 7.3 Hz, 3H), 1.08-1.25 (m, 3 H), 1.32 (dq, J = 14.9, 7.3 Hz, 2H), 1.44-1.65 (m, 6 H), 2.24 (t, J = 5.6 Hz, 1 H), 3.31-3.40 (m, 2 H), 3.42 (s, 1 H), 3.71-3.91 (m, 2 H), 4.25 (d, J = 8.2 Hz, 1 H), 4.31-4.46 (m, 1 H), 4.53 (br. s., 2 H) |
| 27 | 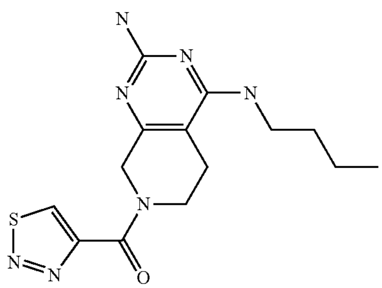 | 333.1 | 334 | ¹H NMR (300 MHz, DMSO-d₆) δ ppm 0.90 (t, J = 7.3 Hz, 3 H), 1.31 (dq, J = 14.9, 7.3 Hz, 2 H), 1.51 (quin, J = 7.3 Hz, 2 H), 2.42 (t, J = 5.2 Hz, 2 H), 3.18-3.28 (m, 2 H), 3.75 (t, J = 5.4 Hz, 1 H), 3.96 (t, J = 5.4 Hz, 1 H), 4.29-4.60 (m, 2 H), 5.65-6.00 (m, 2 H), 6.33-6.66 (m, 1 H), 9.52-9.70 (m, 1 H) |
| 28 | 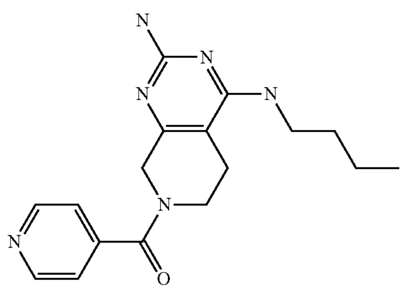 [SMILES: CCCCNc1nc(N)nc2c1CCN(C(=O)c1ccncc1)C2] | 326.2 | 327 | ¹H NMR (300 MHz, DMSO-d₆) δ ppm 0.93 (t, J = 7.3 Hz, 3 H), 1.20-1.43 (m, 5 H), 1.48-1.62 (m, 2H), 2.38 (br. s., 2H), 3.35 (q, J = 6.5 Hz, 1 H), 3.51-3.80 (m, 1H), 4.24 (br.s., 1 H), 5.40 (br. s., 2 H), 6.04 (br. s., 1 H), 7.39 (d, J = 5.8 Hz, 2H), 8.69 (d, J = 5.8 Hz, 2 H) |
| 29 | 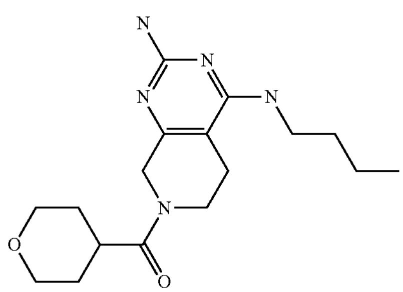 [SMILES: CCCCNc1nc(N)nc2c1CCN(C(=O)C1CCOCC1)C2] | 333.2 | 334 | ¹H NMR (300 MHz, DMSO-d₆) δ ppm 0.92 (t, J = 7.3 Hz, 3 H), 1.19-1.44 (m, 3 H), 1.47-1.77 (m, 6 H), 2.33 (t, J = 5.8 Hz, 2 H), 2.94 (t, J = 4.3 Hz, 2 H), 3.28-3.38 (m, 2 H), 3.44 (td, J = 11.4, 2.4 Hz, 2 H), 3.72 (t, J = 5.9 Hz, 2 H), 3.80-3.93 (m, 2H), 5.38 (br. s., 2 H), 6.00 (br. s., 1 H) |
| 30 | 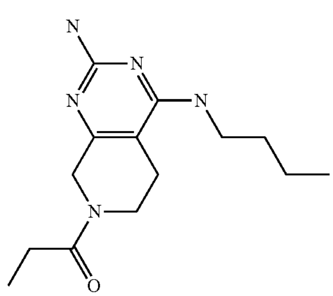 [SMILES: CCCCNc1nc(N)nc2c1CCN(C(=O)CC)C2] | 277.2 | 278 | ¹H NMR (300 MHz, DMSO-d₆) δ ppm 0.90 (t, J = 7.3 Hz, 3 H), 1.00 (q, J = 7.7 Hz, 3 H), 1.19-1.38 (m, 2 H), 1.50 (quin, J = 7.3 Hz, 2 H), 2.23 (t, J = 5.5 Hz, 1 H), 2.27-2.45 (m, 3 H), 3.27 (br. s., 2 H), 3.56-3.73 (m, 2 H), 4.18 (s, 2 H), 5.71 (br. s., 2 H), 6.16-6.42 (m, 1 H) |

TABLE I C-continued

| # | STRUCTURE | Exact Mass | LC-MS (M + H) | NMR |
|---|-----------|-----------|---------------|-----|
| 31 | 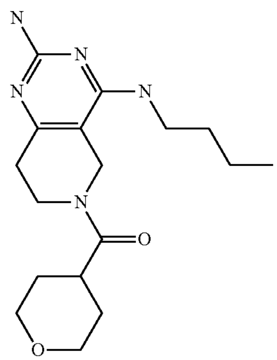 [SMILES: CCCCNc1nc(N)nc2c1CN(C(=O)C1CCOCC1)CC2] | 333.2 | 334 | not available |
| 32 | 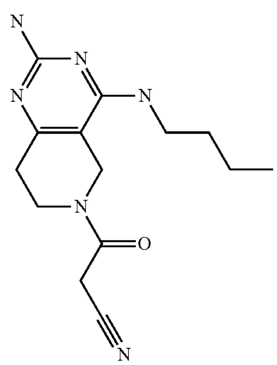 [SMILES: CCCCNc1nc(N)nc2c1CN(C(=O)CC#N)CC2] | 288.2 | 289 | ¹H NMR (300 MHz, DMSO-d₆) δ ppm 0.93 (t, J = 7.3 Hz, 3 H), 1.20-1.43 (m, 4 H), 1.56 (quin, J = 7.3 Hz, 2 H), 3.36 (q, J = 6.2 Hz, 2H), 3.63 (br. s., 2 H), 4.00 (s, 2 H), 4.21 (br. s, 2 H), 5.44 (br. s., 2 H), 6.16 (br. s., 1 H) |
| 33 | 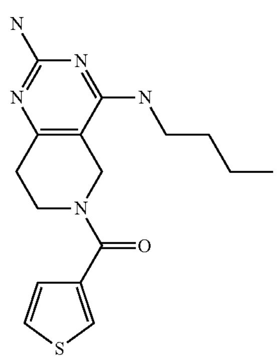 [SMILES: CCCCNc1nc(N)nc2c1CN(C(=O)c1ccsc1)CC2] | 331.1 | 332 | not available |
| 34 | 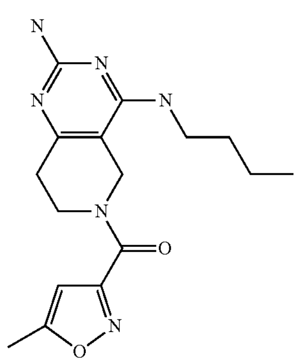 [SMILES: CCCCNc1nc(N)nc2c1CN(C(=O)c1cc(C)on1)CC2] | 330.2 | 331 | ¹H NMR (300 MHz, DMSO-d₆) δ ppm 0.83-0.98 (m, 3 H), 1.22-1.43 (m, 2 H), 1.48-1.65 (m, 2 H), 2.48 (s, 3 H), 3.02-3.07 (m, 2 H), 3.25-3.55 (m, 2 H), 3.64-3.96 (m, 2H), 4.39 (br. s., 2 H), 5.42 (br. s., 2 H), 5.91-6.34 (m, 1 H), 6.36-6.49 (m, 1 H) |

TABLE I C-continued

| # | STRUCTURE | Exact Mass | LC-MS (M + H) | NMR |
|---|---|---|---|---|
| 35 | 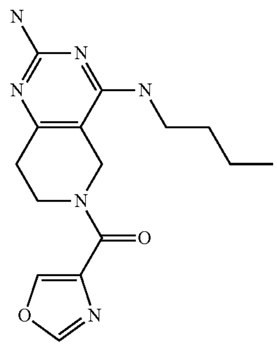 [SMILES: CCCCNc1nc(N)nc2c1CN(C(=O)c1cocn1)CC2] | 316.2 | 317 | ¹H NMR (300 MHz, DMSO-d₆) δ ppm 0.93 (s, 3 H), 1.25-1.46 (m, 2 H), 1.49-1.64 (m, 2 H), 2.53-2.61 (m, 2 H), 3.28-3.44 (m, 2 H), 3.86-4.03 (m, 2 H), 4.30-4.51 (m, 2 H), 5.27-5.52 (m, 2 H), 6.02-6.25 (m, 1 H), 8.39-8.44 (m, 1 H), 8.46-8.50 (m, 1 H) |
| 36 | 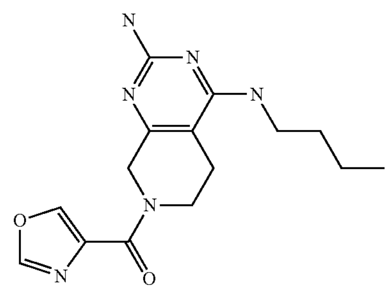 [SMILES: CCCCNc1nc(N)nc2c1CCN(C(=O)c1cocn1)C2] | 316.2 | 317 | ¹H NMR (300 MHz, DMSO-d₆) δ ppm 0.94 (t, J = 7.4 Hz, 3 H), 1.37 (d, J = 7.6 Hz, 2 H), 1.57 (s, 2 H), 2.43 (s, 2 H), 3.37 (d, J = 6.6 Hz, 2 H), 3.98 (br. s., 2 H), 4.52 (br. s., 2 H), 5.42 (br. s., 2 H), 5.97-6.14 (m, 1 H), 8.44 (s, 1 H), 8.50 (s, 1 H) |
| 37 | 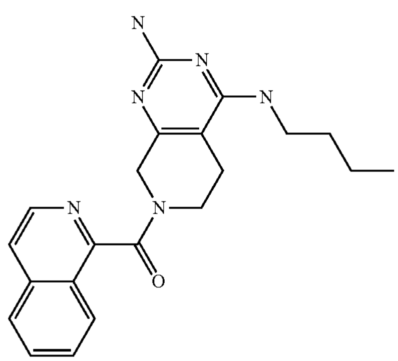 [SMILES: CCCCNc1nc(N)nc2c1CCN(C(=O)c1nccc3ccccc13)C2] | 376.2 | 377 | ¹H NMR (300 MHz, DMSO-d₆) δ ppm 0.82 (d, J = 7.4 Hz, 3 H), 1.11-1.31 (m, 2H), 1.34-1.55 (m, 2 H), 2.07-2.17 (m, 1 H), 3.16-3.21 (m, 2 H), 3.69-3.78 (m, 1 H), 3.87-4.01 (m, 1 H), 4.47 (s, 2 H), 5.43-5.58 (m, 1 H), 5.69-5.80 (m, 2 H), 6.11-6.26 (m, 1 H), 7.54-7.69 (m, 1 H), 7.71-7.91 (m, 1 H), 7.72-7.82 (m, 1 H), 7.84-7.91 (m, 1 H), 7.97-8.06 (m, 1 H), 8.37-8.53 (m, 1 H) |
| 38 | 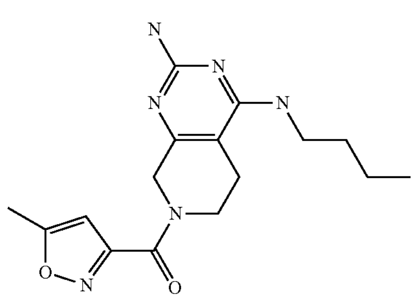 [SMILES: CCCCNc1nc(N)nc2c1CCN(C(=O)c1cc(C)on1)C2] | 330.2 | 331 | ¹H NMR (300 MHz, DMSO-d₆) δ ppm 0.92 (t, J = 7.3 Hz, 3 H), 1.24-1.43 (m, 2 H), 1.55 (t, J = 7.3 Hz, 2 H), 2.40 (t, J = 5.8 Hz, 2 H), 2.48 (s, 3 H), 3.35 (d, J = 6.6 Hz, 2 H), 3.84 (br. s., 2 H), 4.38 (s, 2 H), 5.42 (br. s., 2 H), 5.95-6.19 (m, 1 H), 6.42 (s, 1H) |

TABLE I C-continued

| # | STRUCTURE | Exact Mass | LC-MS (M + H) | NMR |
|---|---|---|---|---|
| 39 | 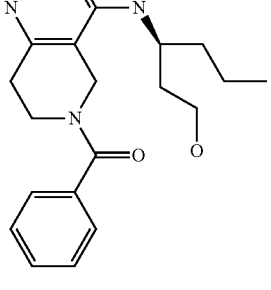 | 369.2 | 370 | $^1$H NMR (300 MHz, DMSO-$d_6$) δ ppm 0.75-0.96 (m, 3 H), 1.14-1.39 (m, 3 H), 1.43-1.79 (m, 5 H), 3.38-3.51 (m, 2 H), 3.55-3.73 (m, 2 H), 3.99-4.16 (m, 1 H), 4.21-4.39 (m, 3 H), 5.32-5.49 (m, 2 H), 5.68-5.83 (m, 1 H), 7.27-7.59 (m, 5 H) |
| 40 | 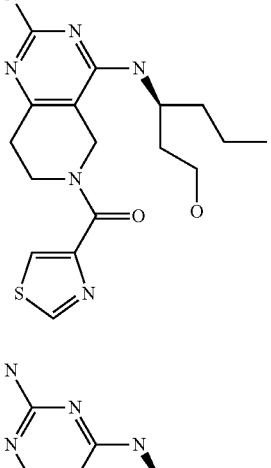 | 376.2 | 377 | $^1$H NMR (300 MHz, DMSO-$d_6$) δ ppm 0.91 (t, J = 7.3 Hz, 3 H), 1.23-1.42 (m, 2 H), 1.54 (d, J = 6.7 Hz, 2 H), 1.66-1.76 (m, 2H), 2.57 (t, J = 5.8 Hz, 2 H), 3.49 (br. s., 2 H), 3.86 (d, J = 5.9 Hz, 1 H), 4.04-4.19 (m, 1 H), 4.22-4.37 (m, 1 H), 4.44 (s, 2 H), 5.43 (br. s., 2 H), 5.70 (s, 1 H), 5.75-5.91 (m, 1 H), 8.13 (d, J = 1.9 Hz, 1 H), 9.15 (d, J = 1.8 Hz, 1 H) |
| 41 | 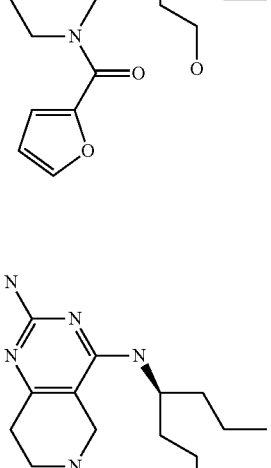 | 359.2 | 360 | $^1$H NMR (300 MHz, DMSO-$d_6$) δ ppm 0.92 (t, J = 7.3 Hz, 3 H), 1.17-1.41 (m, 2 H), 1.57 (dt, J = 14.2, 7.0 Hz, 2 H), 1.66-1.82 (m, 2 H), 2.60 (t, J = 5.8 Hz, 2 H), 3.24 (br. s., 1 H), 3.51 (br. s., 2 H), 3.89 (t, J = 5.9 Hz, 2 H), 4.13 (br. s, 1 H), 4.43 (s, 2 H), 5.43 (s, 2 H), 5.84 (d, J = 8.4 Hz, 1 H), 6.64 (dd, J = 3.2, 1.5 Hz, 1 H), 7.04 (d, J = 3.4 Hz, 1 H), 7.71-7.91 (m, 1 H) |
| 42 | 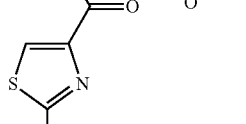 | 390.2 | 391 | $^1$H NMR (300 MHz, DMSO-$d_6$) δ ppm 0.89 (t, J = 7.3 Hz, 3 H), 1.12 (t, J = 7.0 Hz, 1H), 1.24-1.40 (m,2H), 1.44-1.61 (m, 2 H), 1.62-1.78 (m, 2 H), 2.54-2.58 (m, 2 H), 2.71 (s, 3 H), 3.36-3.53 (m, 2 H), 3.85 (q, J = 6.7 Hz, 1 H), 4.11 (br. s., 1 H), 4.20-4.35 (m, 1 H), 4.44 (s, 2 H), 5.40 (br. s., 2 H), 5.78 (d, J = 6.7 Hz, 1 H), 7.87 (s, 1 H) |

TABLE I C-continued

| # | STRUCTURE | Exact Mass | LC-MS (M + H) | NMR |
|---|---|---|---|---|
| 43 | 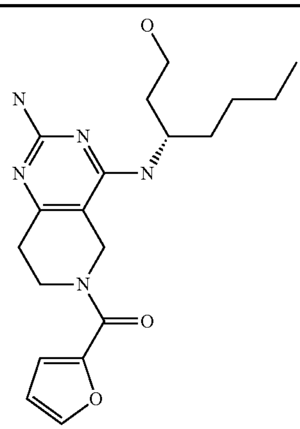 | 373.2 | 374 | ¹H NMR (300 MHz, DMSO-d₆) δ ppm 0.85 (t, J = 6.5 Hz, 3 H), 1.25 (d, J = 4.1 Hz, 4 H), 1.43-1.77 (m, 4 H), 2.57 (br. s, 2 H), 3.40 (q, J = 6.2 Hz, 2 H), 3.74-3.98 (m, 2 H), 4.15-4.30 (m, 1 H), 4.32-4.49 (m, 3 H), 5.80 (br. s, 2 H), 6.17 (br. s., 1 H), 6.66 (dd, J = 3.4, 1.8 Hz, 1 H), 7.08 (d, J = 3.3 Hz, 1 H), 7.86 (d, J = 1.0 Hz, 1 H) |
| 44 | 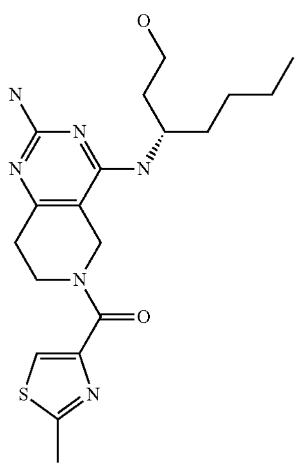 | 404.2 | 405 | ¹H NMR (300 MHz, DMSO-d₆) δ ppm 0.88 (t, J = 6.2 Hz, 3 H), 1.31 (br. s., 4 H), 1.46-1.62 (m, 2H), 1.69 (dt, J = 13.2, 6.6 Hz, 2 H), 2.53-2.59 (m, 2 H), 2.71 (s, 3 H), 3.48 (br. s., 2 H), 3.85 (dq, J = 13.1, 6.8 Hz, 2 H), 4.11 (br. s., 1 H), 4.19-4.34 (m, 1 H), 4.44 (s, 2 H), 5.41 (br. s., 2 H), 5.79 (d, J = 6.7 Hz, 1 H), 7.87 (s, 1 H) |
| 45 | 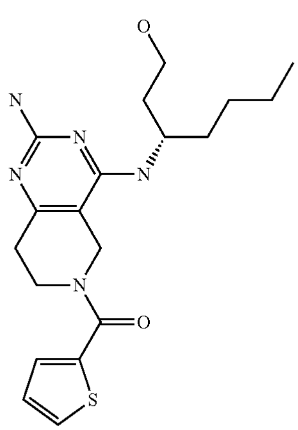 [SMILES: CCCC[C@@H](CCO)Nc1nc(N)nc2c1CN(C(=O)c1ccco1)CC2] | 389.2 | 390 | ¹H NMR (300 MHz, DMSO-d₆) δ ppm 0.87 (t, J = 6.4 Hz, 3 H), 1.29 (d, J = 3.3 Hz, 4 H), 1.45-1.60 (m, 2 H), 1.63-1.79 (m, 2 H), 2.58 (t, J = 5.8 Hz, 2 H), 3.47 (d, J = 4.8 Hz, 2 H), 3.84 (q, J = 6.6 Hz, 2 H), 4.11 (br. s., 1 H), 4.19-4.34 (m, 1 H), 4.42 (s, 2 H), 5.41 (s, 2 H), 5.81 (d, J = 8.4 Hz, 1 H), 7.14 (t, J = 4.3 Hz, 1 H), 7.48 (d, J = 3.6 Hz, 1 H), 7.72 (d, J = 4.9 Hz, 1 H) |

TABLE I C-continued

| # | STRUCTURE | Exact Mass | LC-MS (M + H) | NMR |
|---|---|---|---|---|
| 46 | 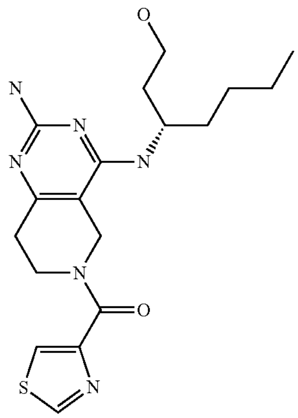 [SMILES: CCCC[C@@H](CCO)Nc1nc(N)nc2c1CN(C(=O)c1cscn1)CC2] | 390.2 | 391 | $^1$H NMR (300 MHz, DMSO-d$_6$) δ ppm 0.80 (t, J = 6.8 Hz, 3 H), 1.11-1.30 (m, 3 H), 1.48 (br. s., 2H), 1.56-1.69 (m, 2 H), 2.48 (t, J = 6.0 Hz, 2 H), 3.13 (d, J = 5.1 Hz, 1 H), 3.39 (d, J = 5.1 Hz, 2 H), 3.76 (d, J = 6.3 Hz, 2 H), 3.93-4.06 (m, 1 H), 4.09-4.24 (m, 1 H), 4.34 (s, 2 H), 5.32 (br. s., 2 H), 5.64-5.80 (m, 1H), 8.03 (d, J = 2.1 Hz, 1 H), 9.05 (d, J = 1.9 Hz, 1 H) |
| 47 | 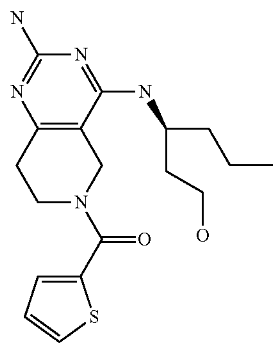 | 375.2 | 376 | $^1$H NMR (300 MHz, DMSO-d$_6$) δ ppm 0.76-0.99 (m, 3 H), 1.16-1.23 (m, 1 H), 1.27-1.39 (m, 2 H), 1.44-1.61 (m, 2 H), 1.65-1.81 (m, 2 H), 2.55-2.62 (m, 2 H), 3.18-3.28 (m, 2 H), 3.41-3.53 (m, 1 H), 3.79-3.92 (m, 2 H), 4.40-4.47 (m, 2 H), 5.34-5.50 (m, 2 H), 5.81-5.89 (m, 1H), 7.10-7.25 (m, 1 H), 7.41-7.54 (m, 1 H), 7.68-7.79 (m, 1 H) |
| 48 | 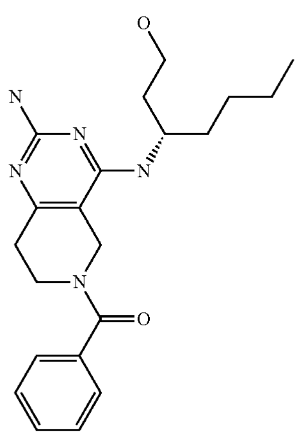 [SMILES: CCCC[C@@H](CCO)Nc1nc(N)nc2c1CN(C(=O)c1ccccc1)CC2] | 383.2 | 384 | $^1$H NMR (300 MHz, DMSO-d$_6$) δ ppm 0.87 (t, J = 6.1 Hz, 3 H), 1.29 (br. s., 4 H), 1.54 (br. s., 2 H), 1.67 (s, 2 H), 2.53 (br. s., 2 H), 3.46 (br. s., 2 H), 3.53-3.77 (m, 2 H), 4.00-4.14 (m, 1 H), 4.20-4.28 (m, 1 H), 4.32 (s, 2 H), 5.40 (br. s., 2 H), 5.67-5.86 (m, 1 H), 7.27-7.53 (m, 5 H) |
| 49 | 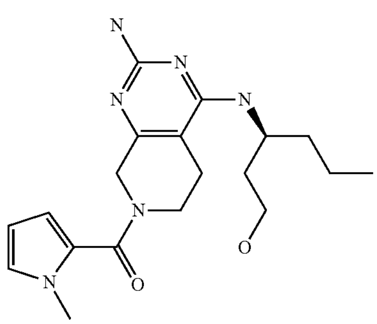 [SMILES: CCC[C@@H](CCO)Nc1nc(N)nc2c1CCN(C(=O)c1cccn1C)C2] | 372.2 | 373 | $^1$H NMR (300 MHz, DMSO-d$_6$) δ ppm 0.70-0.83 (m, 3 H), 1.09-1.29 (m, 3 H), 1.32-1.71 (m, 4 H), 2.26-2.37 (m, 2 H), 3.32-3.40 (m, 2 H), 3.56-3.64 (m, 3 H), 3.71-3.82 (m, 2 H), 4.10-4.22 (m, 1 H), 4.26-4.32 (m, 2 H), 4.33-4.45 (m, 1 H), 5.61-5.74 (m, 1 H), 5.84-5.94 (m, 1 H), 5.96-6.04 (m, 1 H), 6.27-6.36 (m, 1 H), 6.81-6.88 (m, 1 H) |

TABLE I C-continued

| # | STRUCTURE | Exact Mass | LC-MS (M + H) | NMR |
|---|---|---|---|---|
| 50 | 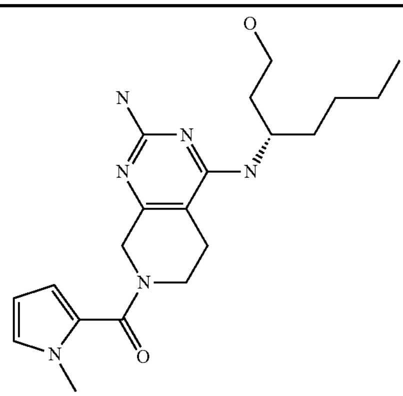 | 386.2 | 387 | $^1$H NMR (300 MHz, DMSO-d$_6$) δ ppm 0.77-0.92 (m, 3 H), 1.13-1.36 (m, 4 H), 1.39-1.74 (m, 4 H), 2.32-2.43 (m, 2 H), 3.38-3.47 (m, 2 H), 3.63-3.71 (m, 3 H), 3.77-3.90 (m, 2 H), 4.17-4.26 (m, 1 H), 4.32-4.38 (m, 2 H), 4.39-4.45 (m, 1 H), 5.65-5.76 (m, 2 H), 5.91-6.01 (m, 1 H), 6.02-6.10 (m, 1 H), 6.34-6.43 (m, 1 H), 6.89-6.95 (m, 1 H) |
| 51 | 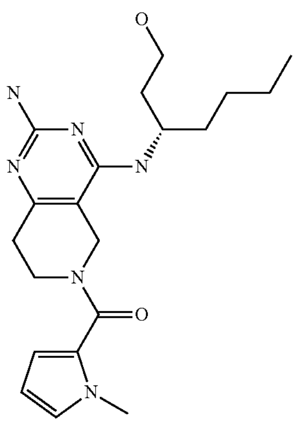 [SMILES: CCCC[C@@H](CCO)Nc1nc(N)nc2c1CN(C(=O)c1cccn1C)CC2] | 386.2 | 387 | $^1$H NMR (300 MHz, DMSO-d$_6$) δ ppm 0.68 (t, J = 6.5 Hz, 3 H), 1.10 (d, J = 3.3 Hz, 4 H), 1.27-1.40 (m, 2 H), 1.49 (dt, J = 13.2, 6.6 Hz, 2 H), 2.33-2.39 (m, 2 H), 3.28 (t, J = 6.2 Hz, 2 H), 3.50 (s, 3 H), 3.54-3.73 (m, 2 H), 3.84-3.97 (m, 1 H), 4.07 (d, J = 7.6 Hz, 1H), 4.18 (s, 2 H), 5.28 (br. s., 2 H), 5.66 (d, J = 8.4 Hz, 1H), 5.81-5.91 (m, 1 H), 6.17 (dd, J = 3.7, 1.5 Hz, 1 H), 6.67 (d, J = 1.6 Hz, 1 H) |
| 52 | 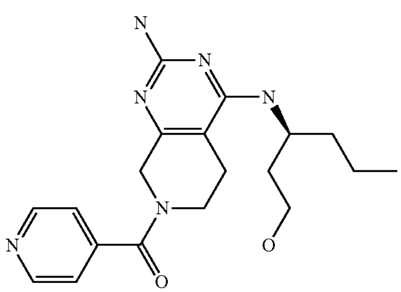 [SMILES: CCC[C@@H](CCO)Nc1nc(N)nc2c1CCN(C(=O)c1ccncc1)C2] | 370.2 | 371 | $^1$H NMR (300 MHz, DMSO-d$_6$) δ ppm 0.80-1.01 (m, 3 H), 1.16-1.39 (m, 3 H), 1.44-1.78 (m, 3 H), 2.26-2.46 (m, 2 H), 3.43-3.56 (m, 2 H), 3.86-3.98 (m, 1 H), 4.06-4.13 (m, 1 H), 4.22-4.34 (m, 1 H), 4.38-4.49 (m, 2 H), 5.64-5.73 (m, 1 H), 5.80-5.89 (m, 2 H), 5.93-6.15 (m, 1 H), 7.40-7.58 (m, 2 H), 8.69-8.81 (m, 2 H) |

Analytical Methods.

All compounds were characterized by LC-MS. The following LC-MS methods were used:

All analyses were performed using an Agilent 1100 series LC/MSD quadrupole coupled to an Agilent 1100 series liquid chromatography (LC) system consisting of a binary pump with degasser, autosampler, thermostated column compartment and diode array detector. The mass spectrometer (MS) was operated with an atmospheric pressure electro-spray ionisation (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software. Analyses were carried out on a YMC pack ODS-AQ C18 column (50 mm×4.6 mm; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

NMR analysis performed using a BRUKER Avance III Spectrometer with a 300 MHz Ultrashield magnet.

Description of Biological Assays

Assessment of TLR7 and TLR8 Activity

The ability of compounds to activate human TLR7 and/or TLR8 was assessed in a cellular reporter assay using HEK293 cells transiently transfected with a TLR7 or TLR8 expression vector and NFκB-luc reporter construct. In one instance the TLR expression construct expresses the respective wild type sequence or a mutant sequence comprising a deletion in the second leucine-rich repeat of the TLR. Such mutant TLR proteins have previously been shown to be more susceptible to agonist activation (U.S. Pat. No. 7,498,409).

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated overnight at 37° C. in a humidified 5% $CO_2$ atmosphere. Transfected cells were then detached with Trypsin-EDTA, washed in PBS and resuspended in medium to a density of $1.67 \times 10^5$ cells/mL. Thirty microliters of cells were then dispensed into each well in 384-well plates, where 10 μL of compound in 4% DMSO was already present. Following 6 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 30 μL per well of cells transfected with the CMV-TLR7 construct alone ($1.67 \times 10^5$ cells/mL), in 384-well plates. Cell viability was measured after 6 hours incubation at 37° C., 5% $CO_2$ by adding 15 μL of ATP lite (Perkin Elmer) per well and reading on a ViewLux ultraHTS microplate imager (Perkin Elmer). Data was reported as $CC_{50}$.

Biological activity of compounds of formula (I). All compounds showed CC50 of >24 uM in the HEK 293 TOX assay described above.

Table 2. Biological Activity of Compounds of Formula (I).

Table II A represent compounds wherein A=NCOR² while Table II B represents compounds wherein B=NCOR⁴ and Table II C contains both region-isomeric compounds respectively.

TABLE II A

| # | STRUCTURE | Human TLR7 (LEC, μM) | Human TLR8 (LEC, μM) |
|---|-----------|----------------------|----------------------|
| 2 | 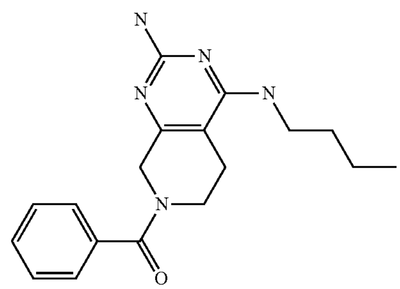 [SMILES: CCCCNc1nc(N)nc2c1CCN(C(=O)c1ccccc1)C2] | 3.96 | 0.75 |
| 3 | 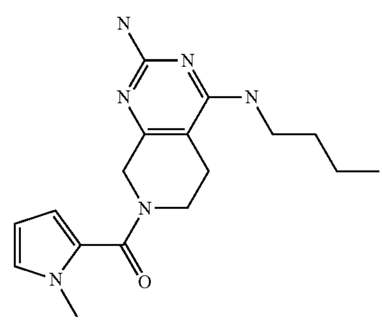 [SMILES: CCCCNc1nc(N)nc2c1CCN(C(=O)c1cccn1C)C2] | 0.79 | 0.60 |
| 4 | 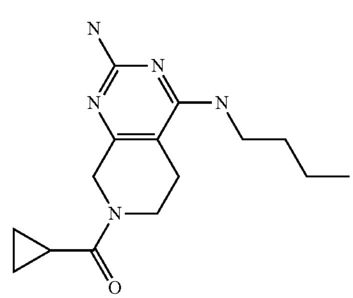 [SMILES: CCCCNc1nc(N)nc2c1CCN(C(=O)C1CC1)C2] | 6.82 | 0.47 |

TABLE II A-continued

| # | STRUCTURE | Human TLR7 (LEC, μM) | Human TLR8 (LEC, μM) |
|---|---|---|---|
| 9 | 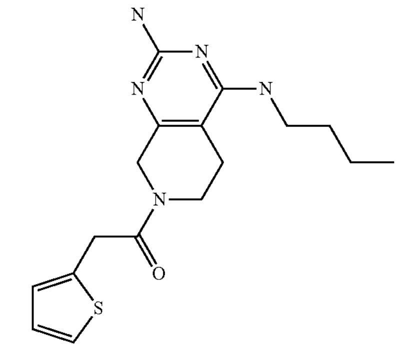 [SMILES: CCCCNc1nc(N)nc2c1CCN(C(=O)Cc1cccs1)C2] | 1.60 | 0.46 |
| 10 | 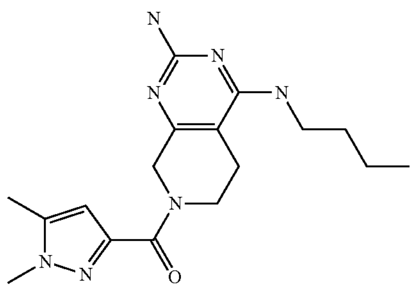 [SMILES: CCCCNc1nc(N)nc2c1CCN(C(=O)c1cc(C)n(C)n1)C2] | 2.04 | 0.71 |
| 11 | 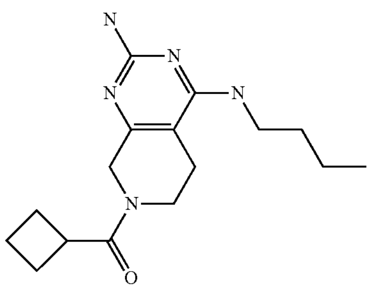 [SMILES: CCCCNc1nc(N)nc2c1CCN(C(=O)C1CCC1)C2] | 2.10 | 0.51 |
| 12 | 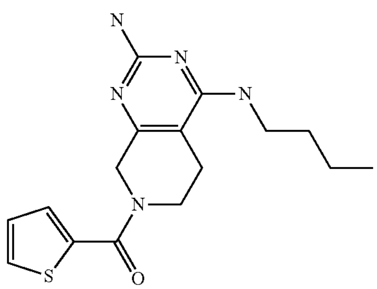 [SMILES: CCCCNc1nc(N)nc2c1CCN(C(=O)c1cccs1)C2] | 2.40 | 0.36 |
| 13 | 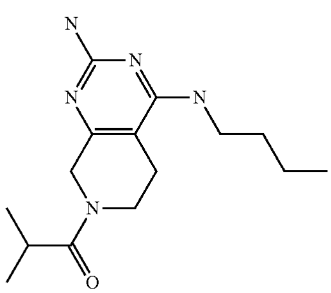 | 3.21 | 0.85 |

TABLE II A-continued

| # | STRUCTURE | Human TLR7 (LEC, μM) | Human TLR8 (LEC, μM) |
|---|---|---|---|
| 14 | 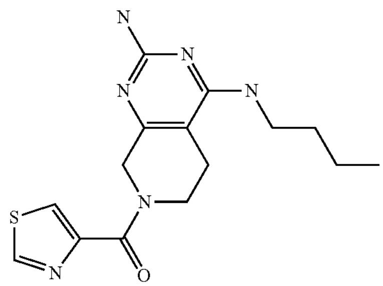 [SMILES: CCCCNc1nc(N)nc2c1CCN(C(=O)c1cscn1)C2] | 4.43 | 0.90 |
| 15 | 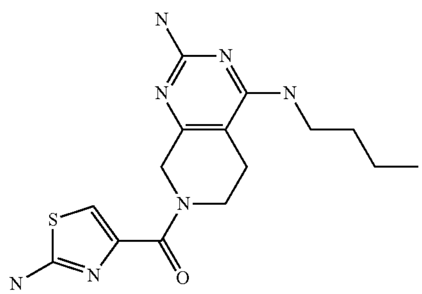 [SMILES: CCCCNc1nc(N)nc2c1CCN(C(=O)c1csc(N)n1)C2] | 4.66 | 1.31 |
| 16 | 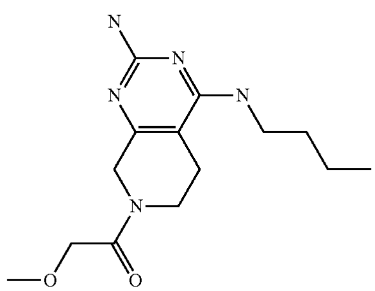 [SMILES: CCCCNc1nc(N)nc2c1CCN(C(=O)COC)C2] | 5.37 | 1.49 |
| 17 | 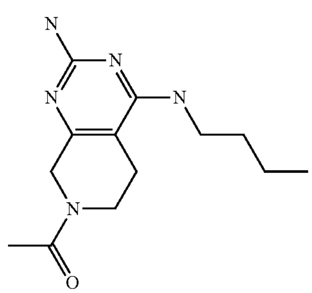 [SMILES: CCCCNc1nc(N)nc2c1CCN(C(C)=O)C2] | 5.82 | 0.43 |
| 18 | 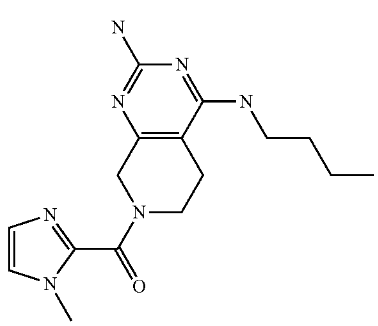 [SMILES: CCCCNc1nc(N)nc2c1CCN(C(=O)c1nccn1C)C2] | 6.16 | 0.96 |

TABLE II A-continued

| # | STRUCTURE | Human TLR7 (LEC, μM) | Human TLR8 (LEC, μM) |
|---|---|---|---|
| 19 | 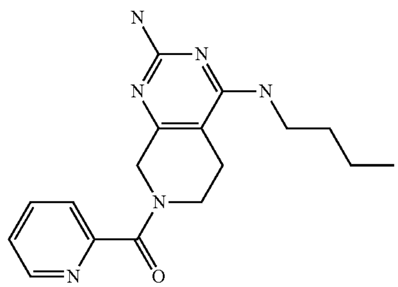 | 6.59 | 0.83 |
| 20 | 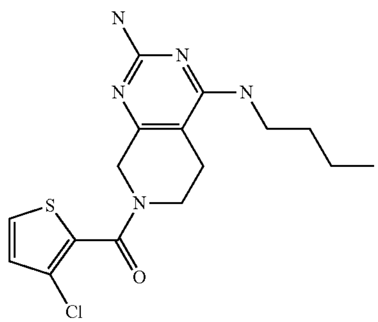 [SMILES: CCCCNc1nc(N)nc2c1CCN(C(=O)c1sccc1Cl)C2] | 7.15 | 0.68 |
| 21 | 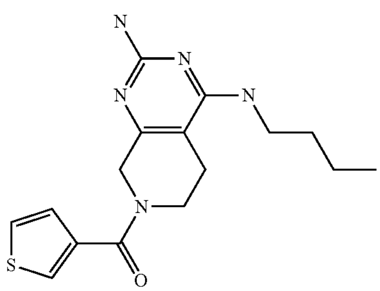 [SMILES: CCCCNc1nc(N)nc2c1CCN(C(=O)c1ccsc1)C2] | 8.13 | 1.85 |
| 22 | 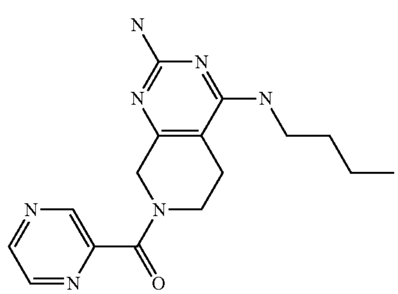 | 9.35 | 1.37 |
| 23 | 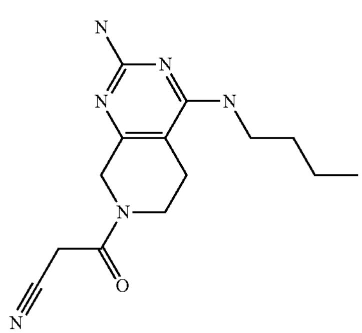 [SMILES: CCCCNc1nc(N)nc2c1CCN(C(=O)CC#N)C2] | 11.62 | 2.67 |

TABLE II A-continued

| # | STRUCTURE | Human TLR7 (LEC, μM) | Human TLR8 (LEC, μM) |
|---|---|---|---|
| 24 | (structure) | 12.93 | 2.29 |

TABLE II B

| # | STRUCTURE | Human TLR7 (LEC, μM) | Human TLR8 (LEC, μM) |
|---|---|---|---|
| 1 | (structure) | 0.83 | 0.32 |
| 5 | (structure) | 4.90 | 0.50 |
| 6 | (structure) | 3.45 | 0.88 |
| 7 | (structure) | 8.13 | 1.62 |
| 8 | (structure) | 2.34 | 0.40 |

TABLE II C

| # | Human TLR7 (LEC, μM) | Human TLR8 (LEC, μM) | PBMC-IFNa (LEC, μM) |
|---|---|---|---|
| 25 | 20.0 | 1.8 | 1.1 |
| 26 | 16.8 | 2.1 | 0.6 |
| 27 | >25 | 1.9 | 1.2 |
| 28 | 8.6 | 2.2 | 1.9 |
| 29 | >25 | 7.5 | 8.7 |
| 30 | 5.0 | 0.5 | 0.5 |
| 31 | 7.7 | 0.6 | 1.3 |
| 32 | 7.1 | 0.6 | 0.9 |
| 33 | 0.3 | 0.2 | 0.2 |
| 34 | 0.8 | 0.4 | 0.2 |
| 35 | 0.7 | 0.2 | 0.2 |
| 36 | 4.7 | 0.9 | 0.6 |
| 37 | 7.2 | 1.7 | 1.8 |
| 38 | 5.2 | 0.8 | 0.6 |
| 39 | 2.5 | 4.2 | 0.5 |

57

TABLE II C-continued

| # | Human TLR7 (LEC, μM) | Human TLR8 (LEC, μM) | PBMC-IFNa (LEC, μM) |
|---|---|---|---|
| 40 | 2.2 | 4.5 | 0.2 |
| 41 | 0.4 | 0.4 | 0.1 |
| 42 | 2.2 | 2.1 | 0.2 |
| 43 | 0.1 | 0.7 | 0.04 |
| 44 | 1.0 | 6.6 | 0.2 |
| 45 | 0.2 | 1.7 | 0.2 |
| 46 | 0.6 | 3.5 | 0.2 |
| 47 | 0.2 | 1.1 | 0.2 |
| 48 | 1.2 | 3.9 | 0.3 |
| 49 | 2.7 | 4.0 | 0.3 |
| 50 | 1.7 | 3.9 | 0.3 |
| 51 | 0.5 | 0.4 | 0.1 |
| 52 | 12.1 | 15 | NA |

The invention claimed is:

1. A compound of formula (I)

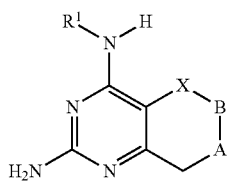

(I)

or a pharmaceutically acceptable salt, tautomer, or solvate thereof, wherein

A is selected from the group consisting of $CH_2$, $NCOR^2$, $CHR^3$ and $CR^3R^3$ in any stereo chemical configuration, B is selected from the group consisting of $CH_2$, $NCOR^4$, $CHR^3$ and $CR^3R^3$ in any stereo chemical configuration, with the proviso that when A is $NCOR^2$ then B is not $NCOR^4$ and with the proviso that A and B are not both selected from $CH_2$, $CHR^3$ or $CR^3R^3$, X is selected from $CH_2$ or $CHR^5$ in any stereo chemical configuration, $R^1$ is selected from $C_{1-8}$alkyl optionally substituted with one or more of the following: $C_{1-6}$alkyl, $C_{3-7}$cycloalkyl, hydroxyl, hydroxyalkyl, amino, nitrile, alkoxy and alkoxy-$(C_{1-4})$alkyl, $R^2$ is selected from substituted and unsubstituted $C_{1-6}$alkyl, $C_{3-7}$cycloalkyl, heterocycle, aryl, heteroaryl, heteroarylalkyl, each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkoxy, $C_{3-6}$cycloalkyl, heterocycle, aryl, alkenyl, alkynyl, arylalkyl, heteroaryl, heteroarylalkyl or nitrile, $R^3$ is selected from hydrogen, substituted and unsubstituted $C_{1-6}$alkyl, alkoxy, alkoxy-$(C_{1-4})$alkyl, $C_{3-7}$cycloalkyl, $C_{4-7}$heterocycle, aromatic, bicyclic heterocycle, arylalkyl, heteroaryl, heteroarylalkyl each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$alkoxy, $C_{3-6}$cycloalkyl, heterocycle, aryl, alkenyl, alkynyl, arylalkyl, heteroaryl, heteroarylalkyl or nitrile, $R^4$ is selected from substituted or unsubstituted alkoxy, alkoxy-$(C_{1-4})$alkyl, aryl or $C_{3-7}$cycloalkyl each of which is optionally substituted by heterocycle, nitrile, heteroarylalkyl or heteroaryl and wherein $R^5$ is selected from aromatic, bicyclic heterocycle, aryl, heteroaryl, each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$alkoxy, $C_{3-6}$cycloalkyl, heterocycle, aryl, alkenyl, alkynyl, arylalkyl, heteroaryl, heteroarylalkyl or nitrile.

2. A compound of formula (I) as claimed in claim 1 wherein $R^1$ is butyl.

3. A compound of formula (I) as claimed in claim 1 wherein $R^1$ is $C_{4-8}$alkyl substituted with hydroxyl.

4. A compound of formula (I) as claimed in claim 3 wherein $R^1$ selected from the group consisting of:

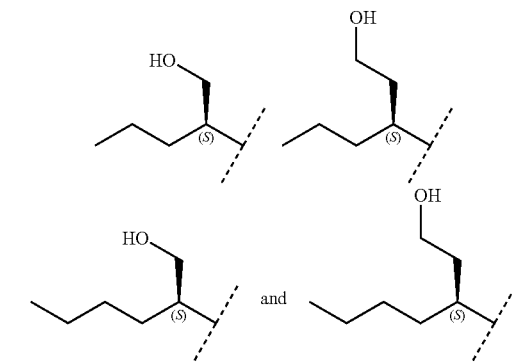

5. A compound of formula (I) as claimed in claim 1 wherein X is $CH_2$.

6. A compound of formula (I) as claimed in claim 1 wherein X is $CH_2$ and A is $CH_2$.

7. A pharmaceutical composition comprising a compound of formula (I) or a pharmaceutically acceptable salt, tautomer or solvate thereof as claimed in claim 1 together with one or more pharmaceutically acceptable excipients, diluents or carriers.

* * * * *